(12) United States Patent
Franzen et al.

(10) Patent No.: US 7,868,161 B2
(45) Date of Patent: Jan. 11, 2011

(54) PHOTOCROSSLINKING PROBES AND USES OF THE SAME

(75) Inventors: Stefan Franzen, Apex, NC (US); Bohdan Skalski, Poznan (PL)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/496,264

(22) Filed: Jul. 31, 2006

(65) Prior Publication Data

US 2007/0082349 A1 Apr. 12, 2007

Related U.S. Application Data

(60) Provisional application No. 60/703,819, filed on Jul. 29, 2005.

(51) Int. Cl.
C07H 21/00 (2006.01)
C07H 21/04 (2006.01)
(52) U.S. Cl. .................. 536/25.3; 536/24.3
(58) Field of Classification Search ............ None
See application file for complete search history.

(56) References Cited

U.S. PATENT DOCUMENTS

| | | | |
|---|---|---|---|
| 4,826,967 A | 5/1989 | Glass | |
| 4,973,679 A | 11/1990 | Caruthers et al. | |
| 5,026,838 A | 6/1991 | Nojiri et al. | |
| 5,082,934 A | 1/1992 | Saba et al. | |
| 5,142,047 A | 8/1992 | Summerton et al. | |
| 6,303,799 B1 | 10/2001 | Cheng et al. | |
| 6,482,594 B2 | 11/2002 | Gold et al. | |
| 2003/0143581 A1 | 7/2003 | Franzen et al. | |
| 2003/0147966 A1 | 8/2003 | Franzen et al. | |
| 2003/0157725 A1 | 8/2003 | Franzen et al. | |
| 2004/0180369 A1 | 9/2004 | Franzen et al. | |
| 2007/0082349 A1 | 4/2007 | Franzen et al. | |

FOREIGN PATENT DOCUMENTS

| WO | WO 96/28438 | 9/1996 |
|---|---|---|
| WO | WO 02/077262 | * 10/2002 |
| WO | WO2005/042783 | 5/2005 |
| WO | WO2005/042785 | 5/2005 |
| WO | WO2007/014348 | 2/2007 |

OTHER PUBLICATIONS

Lehninger, Biochemistry, Second Edition, 1975, Worth Publishers, New York, NY, p. 311.*
Wenska et al., Photochemical transformations of 5-halogeno-4-thiouridines, J. Chem. Soc., Perkin Trans. 1, 2002, 53-57.*

(Continued)

Primary Examiner—Mark Staples
(74) Attorney, Agent, or Firm—Jenkins, Wilson, Taylor & Hunt, P.A.

(57) ABSTRACT

A method of detecting a target nucleic acid is disclosed, the method comprising detecting the presence of a fluorescent covalent crosslinked product from non-fluorescent precursors. The fluorescent covalent crosslinked product comprises a novel fluorophore structure. Also described are methods of synthesizing probe molecules that can form fluorescent covalent crosslinked products with nucleic acid targets and arrays comprising such probes.

42 Claims, 24 Drawing Sheets

OTHER PUBLICATIONS

Favre et al., Thionucleobases as intrinsic photoaffinity probes of nucleic acid structure and nucleic acid-protein interactions, Journal of Photochemistry and Photobiology B: Biology 42 (1998) 1109-1124.*

Kumar et al., Synthesis and studies on the effect of 2-thiouridine and 4-thiouridine on sugar conformation and RNA duplex stabilityNucleic Acids Research, 1997, vol. 25, No. 6, pp. 1272-1280.*

Chaput et al., TNA Synthesis by DNA Polymerases, J. Am. Chem. Soc. 2003, 125, 9274-9275.*

Coleman et al., Synthesis and Postsynthetic Modification of Oligodeoxynucleotides Containing 4-Thio-2'-deoxyuridine (ds4U), J. Am. Chem. Soc. 1994,116, 11636-11642.*

Skaski and Franzen et al., Photoinduced Fluorescent Cross-Linking of 5-Chloro- and 5-Fluoro-4-thiouridines with Thymidine, J. Org. Chem. 2010, 75, 621-626.*

Notification of the International Search Report and the Written Opinion of the International Searching Authority, or the Declaration corresponding to the PCT Application No. PCT/US06/29545 dated Apr. 3, 2007.

Skalski et al. Fluorolink: A fluorophore created by a photocrosslinking reaction in DNA/RNA hybrids. Abstract for Oral Presentation No. 143C on Aug. 29, 2005, The 230$^{th}$ ACS National Meeting held in Washington D.C., Aug. 28-Sep. 1, 2005.

Masternak et al. *Solvatochromism of a Novel betaine dye derived from purine. Journal of Physical Chemistry A*, vol. 109, (2005), pp. 759-766.

Jarmula et al. Relative free energies of binding to thymidylate synthase of 2- and/or 4-thio and/or 5-fluoro analogues of dUMP. Journal of Computer-Aided Molecular Design, vol. 17, (2003), pp. 699-710.

Coleman, R.S. and Siedlecki, J.M., Synthesis of a 4-Thio-2'-deoxyuridine-Containing Oligonucleotide. Development of the Thiocarbonyl Group as a Linker Element. *Journal of the American Chemical Society*. vol. 114 pp. 9229-9230 (1992).

Norris et al., Mechanistic Studies of the 5-Iodouracil Chromophore Relevant to Its Use in Nucleoprotein Photo-Cross-Linking. *Journal of the American Chemical Society*. vol. 118 pp. 5796-5803 (1996).

Skalski et al., Photochemistry of 5-Fluoro-4-Thiouridine-Containing Double Stranded DNA/RNA Oligonucleotide Constructs. *21$^{st}$ International Conference of Photochemistry*. Nara, Japan. Jul. 26-31, 2003. Book of Abstracts. [Abstract].

Tara-Goślińska et al., Spectral and photophysical properties of the lowest excited triplet state of 4-thiouridine and its 5-halogeno derivatives. *Journal of Photochemistry and Photobiology A: Chemistry*. vol. 168 pp. 227-233 (2004).

Wenska et al., Generation of Thiyl Radicals by the Photolysis of 5-Iodo-4-thiouridine. *Journal of Organic Chemistry*. vol. 70 pp. 982-988 (2005).

Notification Concerning Transmittal of International Preliminary Report on Patentability (Chapter I of the Patent Cooperation Treaty) corresponding to International Application No. PCT/US2006/029545 dated Feb. 7, 2008.

* cited by examiner

A

B

PHOTOCROSSLINKING PROBES AND USES OF THE SAME

CROSS REFERENCE TO RELATED APPLICATIONS

This application claims the benefit of and priority to U.S. Provisional Patent Application Ser. No. 60/703,819, filed Jul. 29, 2005, the disclosure of which is incorporated herein by reference in its entirety.

TECHNICAL FIELD

The presently disclosed subject matter relates generally to methods of and compositions for detecting target nucleic acids in a sample by detecting the presence of a fluorescent crosslinked product from non-fluorescent precursors. The fluorescent product can be a crosslinked photoproduct. The presently disclosed subject matter also generally relates to methods of synthesizing oligonucleotide probes that form fluorescent crosslinked products and photoproducts, to arrays of such probes, and to the fluorophore structure of the fluorescent crosslinked photoproduct itself.

ABBREVIATIONS

δ=chemical shift
° C.=degrees Celsius
1-D=one-dimensional
2-D=two-dimensional
4tU=4-thiouridine
A=adenine
BrU=5-bromouridine
C=cytosine
DFT=density function theory
DNA=deoxyribonucleic acid
FISH=fluorescent in-situ hybridization
FSU=5-fluoro-4-thiouridine
G=guanine
Hg=mercury
HMBC=heteronuclear multiple bond correlation
HPLC=high pressure liquid chromatography
HSQC=heteronuclear single quantum correlation
kJ=kilojoules
m=meter
mM=millimolar
MALDI=matrix assisted laser desorption ionization
nm=nanometers
ns=nanoseconds
NMR=nuclear magnetic resonance
NOE=nuclear overhauser effect
ns=nanosecond
PAGE=polyacrylamide gel electrophoresis
PCR=polymerase chain reaction
ppm=parts per million
T=thymine
TBAHS=tetrabutylammonium hydrogen sulfate
TOF=time-of-flight
U=uracil
UV=ultraviolet
W=watts

BACKGROUND

Crosslinking compounds based on furocoumarin (or psoralen) are disclosed in U.S. Pat. No. 4,826,967 to Glass. The compounds are attached to existing polynucleotides, usually through adduct formation. Psoralen is fluorescent with emission in the range of 450-500 nm with a low quantum yield of less than $10^{-2}$ in the uncrosslinked state. The crosslinked psoralen photoproduct, however, has greatly reduced fluorescence. See "Bioorganic Photochemistry: Photochemistry of the Nucleic Acids," Vol. 1, Morrison, H., ed., Wiley and Sons, New York, 1990.

U.S. Pat. No. 5,082,934 to Saba et al. discloses a nucleoside analogue comprising a coumarin moiety linked through its phenyl ring to the 1-position of a ribose or deoxyribose sugar moiety in the absence of an intervening base moiety. The resulting nucleoside analogue is used as a crosslinking group when inserted into a polynucleotide as a replacement for one or more of the complementary nucleoside bases present in a probe used in hybridization assays. The sugar moiety, however, limits the conformational flexibility of the crosslinking group.

PCT Publication Number WO96/28438 to Wood et al. discloses non-nucleosidic coumarin derivatives wherein the coumarin moiety is joined within the backbone of an oligonucleotide probe via moieties other than deoxyribose or ribose.

Additionally, U.S. Pat. No. 6,303,799 to Cheng et al. discloses aryl olefins as crosslinking groups in oligonucleotide probes for use in hybridization-based assays and as therapeutic agents.

With the ever-increasing use of oligonucleotide probe technology in biological and medical research, there remains a need for additional cross-linking probes. In particular, there is an outstanding need for additional cross-linking probes that would facilitate the detection of the cross-linked products or photoproducts of the probes and their nucleic acid targets. Such probes could have application in cellular assays to determine the genotype or presence of an infectious agent and in oligonucleotide arrays for the quantification of oligonucleotides in a sample obtained from a living cell.

SUMMARY

In some embodiments, the presently disclosed subject matter provides a method of determining the presence of a target nucleic acid molecule in a sample, the method comprising detecting a fluorescent covalent crosslinked product formed between a probe molecule and the target nucleic acid, the fluorescent covalent crosslinked product comprising a structure of Formula (I):

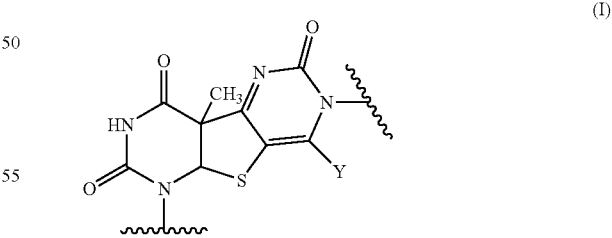

wherein:
Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and $R_4$ are selected from H and $C_1$-$C_5$ alkyl.

In some embodiments, the fluorescent covalent crosslinked product is formed following photoexcitation of the probe molecule.

In some embodiments, the probe molecule comprises an oligonucleotide sequence comprising one or more 5-halo-4-thiouracil nucleobases.

In some embodiments, the method comprises:
(a) contacting the probe molecule with the sample comprising the target nucleic acid, wherein the probe molecule hybridizes to the target nucleic acid in the sample to form an oligonucleotide duplex;
(b) irradiating the oligonucleotide duplex for a period of time to form one or more covalent bonds between the probe molecule and the target nucleic acid to form the fluorescent crosslinked product; and
(c) detecting fluorescence of the fluorescent crosslinked product at a chosen emission wavelength, thereby determining the presence of a target nucleic acid molecule in the sample.

In some embodiments, each of the one or more 5-halo-4-thiouracil nucleobases comprises a structure of formula (II):

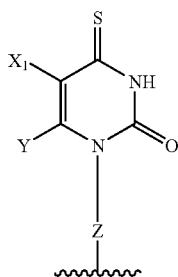

(II)

wherein:

$X_1$ is halo;

Y is selected from the group consisting of H, $C_1$-$C_5$ linear or branched alkyl, cyano, nitro, carboxy, —$NR_1R_2$, —C(O)$R_3$, and —NH—C(O)—$R_4$, wherein $R_1$, $R_2$, $R_3$, and $R_4$ are selected from H and $C_1$-$C_5$ alkyl; and Z is selected from the group consisting of ribose, 2'-deoxyribose, 2'-O-methyl ribose and morpholino.

In some embodiments, Y is H and $X_1$ is selected from fluoro and chloro. In some embodiments, Z is ribose and each of the one or more 5-halo-4-thiouracil nucleobases are independently a 5-fluoro-4-thiouridine residue or a 5-chloro-4-thiouridine residue. The molecule in Formula II has an extremely low fluorescent quantum yield. Extremely weak phosphorescence emission is observed at much longer wavelengths that do not interfere with the fluorescence detection applications described herein.

In some embodiments, at least one of the one or more 5-halo-4-thiouracil nucleobases is located adjacent to at least one adenine residue in the oligonucleotide sequence of the probe molecule.

In some embodiments, the contacting step takes place in a cell. In some embodiments, both the probe molecule and the target nucleic acid are in solution. In some embodiments, either the target nucleic acid or the probe molecule is immobilized on a solid support. In some embodiments, the solid support is selected from the group consisting of a flat surface, a bead, a resin, a gel, a microsphere, a well, a microtiter plate, and a fiber.

In some embodiments, the method of detecting a target nucleic acid further comprises determining an amount of the target nucleic acid in the sample. In some embodiments, the method further comprises separating the oligonucleotide duplex containing the fluorescent covalent crosslinked product from non-duplexed nucleic acids and probe molecules following the irradiating step.

In some embodiments, there is zero background fluorescence at the chosen emission wavelength prior to performing the irradiation step.

In some embodiments, the irradiating step is performed at a wavelength longer than about 280 nanometers. In some embodiments, the irradiating step is performed with a UV light source.

In some embodiments, the method further comprises amplifying one or more nucleic acid in the sample prior to contacting the probe molecule with the sample.

In some embodiments, the oligonucleotide sequence of the probe molecule is at least 70% complementary to the target nucleic acid.

In some embodiments, the oligonucleotide sequence of the probe molecule is 10 or more nucleotides in length. In some embodiments, the oligonucleotide sequence of the probe molecule is 10 to 50 nucleotides in length. In some embodiments, the oligonucleotide sequence of the probe molecule is 50 to 100 nucleotides in length. In some embodiments, the oligonucleotide sequence of the probe molecule is greater than 100 nucleotides in length.

In some embodiments, the target nucleic acid is selected from the group consisting of animal, bacterial, fungal, human, parasitic, plant and viral nucleic acids. In some embodiments, the target nucleic acid is selected from the group consisting of genomic DNA and cDNA. In some embodiments, the method of determining the presence of a target nucleic acid determines the presence of a gene or of foreign DNA in a cell.

In some embodiments, the target nucleic acid is selected from the group consisting of tRNA, rRNA, mRNA, microRNA and a non-coding RNA. In some embodiments, the sample is selected from the group consisting of a biological sample and an environmental sample. In some embodiments the sample is a biological sample selected from the group consisting of a living cell, a fixed cell, a cell extract, a tissue, a tissue extract, blood, plasma, saliva, and urine. In some embodiments, the biological sample is from a mammalian subject. In some embodiments, the sample is an environmental sample selected from the group consisting of tap water, waste water, well water, river water, lake water, soil, air and material collected from household surfaces.

In some embodiments, determining the presence of a target nucleic acid is indicative of one of the presence of a disease, the absence of a disease, the potential future presence of a disease, the progression of a disease, the regression of a disease, and combinations thereof. In some embodiments determining the presence of a target nucleic acid is indicative of the presence of one of the group consisting of a virus, a bacteria, a fungus, a parasite, and combinations thereof.

In some embodiments, the method comprises one or more target nucleic acids in a sample using two or more probe molecules, wherein each of the two or more probe molecules comprises an oligonucleotide sequence at least 70% complementary to a different target nucleic acid.

In some embodiments, the presently disclosed subject matter provides a method of synthesizing a probe molecule that forms a fluorescent covalent crosslinked product with a target nucleic acid, wherein the fluorescent covalent crosslinked product has a structure of Formula (I):

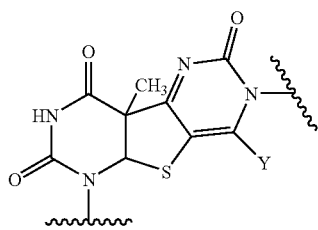

(I)

wherein:

Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and R4 are selected from H and $C_1$-$C_5$ alkyl;

the method comprising incorporating into an oligonucleotide sequence one or more nucleotide synthons having a structure of Formula (III):

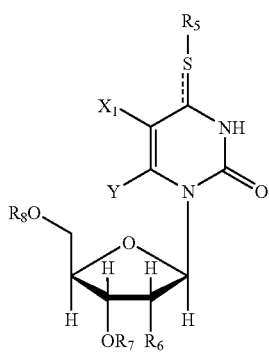

(III)

wherein:

$X_1$ is halo;

Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and $R_4$ are selected from H and $C_1$-$C_5$ alkyl;

$R_5$ is present or absent, and when present is a suitable sulfur protecting group;

$R_6$ is selected from the group consisting of H, hydroxy, and —$OR_{10}$, wherein $R_{10}$ is alkyl or a suitable hydroxyl protecting group;

$R_7$ is selected from the group consisting of

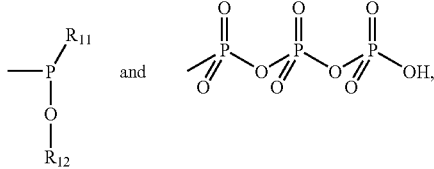

wherein $R_{11}$ is a secondary amino group; and $R_{12}$ is selected from the group consisting of allyl and —$CH_2CH_2R_{13}$, wherein $R_{13}$ is selected from the group consisting of cyano, nitro, halo, thiocyano, alkylsulfonate, and arylsulfonate; and $R_8$ is selected from the group consisting of H and a suitable hydroxyl protecting group.

In some embodiments, $R_5$ is present and is selected from the group consisting of —$CH_2CH_2R_9$, wherein $R_9$ is selected from cyano, nitro, halo, thiocyano, alkylsulfonate, and arylsulfonate.

In some embodiments, $R_{10}$ is trialkylsilyl. In some embodiments, $R_{10}$ is t-butyldimethylsilyl.

In some embodiments, $R_8$ is selected from trityl, monomethoxytrityl, dimethoxytrityl, trimethylsilyl, triethylsilyl, triphenylsilyl, t-butyldimethylsilyl, tetrahydropyranyl, 4-methoxyhydrofuranyl, benzoyl, benzyl, tetrahydrofuranyl, methoxymethyl, methoxyethoxymethyl, phenoxymethyl, methylthiomethyl, and phenylthiomethyl.

In some embodiments, the synthesizing comprises the use of phorphoramidite chemistry and $R_7$ is

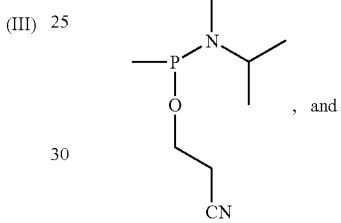

, and $R_8$ is

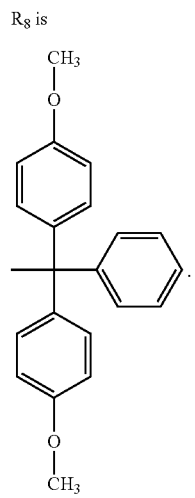

In some embodiments, the synthesizing is enzymatically catalyzed and $R_7$ is

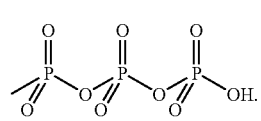

In some embodiments, the presently disclosed subject matter provides an array for determining the presence of one or more target nucleic acids by detecting the presence of a fluorescent crosslinked product, said fluorescent crosslinked product comprising a structure of Formula (I):

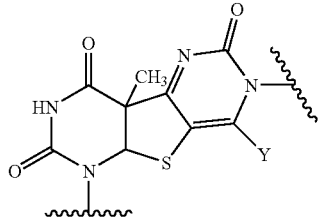

wherein:
Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and $R_4$ are selected from H and $C_1$-$C_5$ alkyl;

wherein the array comprises:
(a) a solid support; and
(b) a probe set comprising two or more probe molecules, each probe molecule comprising an oligonucleotide sequence comprising one or more 5-halo-4-thiouracil nucleobases, wherein:
 (i) each of the two or more probe molecules comprises an oligonucleotide sequence at least 70% complementary to a different target nucleic acid sequence; and
 (ii) the two or more probe molecules are immobilized on the solid support.

In some embodiments, each of the two or more probe molecules is immobilized at a different discrete, known location on the solid support.

In some embodiments, the presently disclosed subject matter provides a fluorophore comprising a structure of Formula (I):

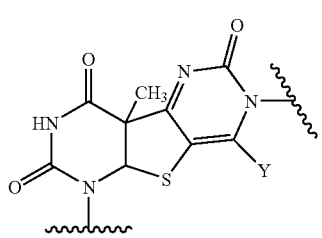

wherein:
Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and $R_4$ are selected from H and $C_1$-$C_5$ alkyl.

In some embodiments, the fluorophore having a structure of Formula (I) has a structure of Formula (Ia):

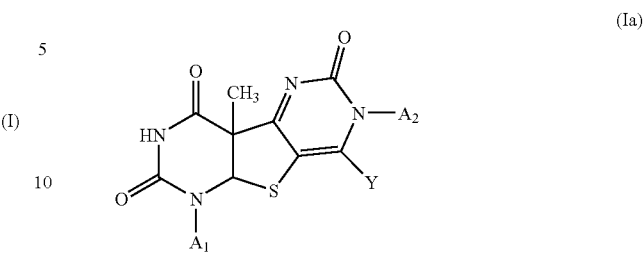

wherein:
Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and $R_4$ are selected from H and $C_1$-$C_5$ alkyl;
$A_1$ is selected from a sugar, a protected sugar, a partially protected sugar, and a nucleic acid; and
$A_2$ is selected from a sugar, a protected sugar, a partially protected sugar, and an oligonucleotide.

In some embodiments, $A_1$ is a gene or a cDNA, and $A_2$ is an oligonucleotide. In some embodiments, $A_1$ and $A_2$ are at least 70% complementary.

In some embodiments, the fluorophore is formed following irradiation of a fluorophore precursor comprising a hybridized duplex. In some embodiments, the hybridized duplex comprises an oligonucleotide comprising one or more 5-halo-4-thiouracil nucleobases, each of which is adjacent to one or more adenine residues.

Accordingly, it is an object of the presently disclosed subject matter to provide a method of detecting a target nucleic acid in a sample by detecting the presence of a fluorescent covalent crosslinked product having a structure of Formula (I).

It is another object of the presently disclosed subject matter to provide a method of synthesizing a probe molecule that forms a fluorescent covalent crosslinked product, wherein the fluorescent covalent crosslinked product has a structure of Formula (I), by incorporating into an oligonucleotide sequence one or more nucleotide synthons having a structure of Formula (III).

It is another object of the presently disclosed subject matter to provide an array for determining the presence of one or more target nucleic acids by detecting the presence of a fluorescent covalent crosslinked product having a structure of Formula (I).

It is another object of the presently disclosed subject matter to provide a fluorophore comprising a structure of Formula (I) or Formula (Ia).

Certain objects of the presently disclosed subject matter having been stated hereinabove, which are addressed in whole or in part by the presently disclosed subject matter, other objects and advantages will become apparent to those of ordinary skill in the art after a study of the following description of the presently disclosed subject matter and in the accompanying non-limiting Examples.

The darker line showing greater absorption at 330 nm corresponds to the spectra of the hybrid at 60° C., while the other line shows the spectra of the hybrid at 15° C.

Figure 7:
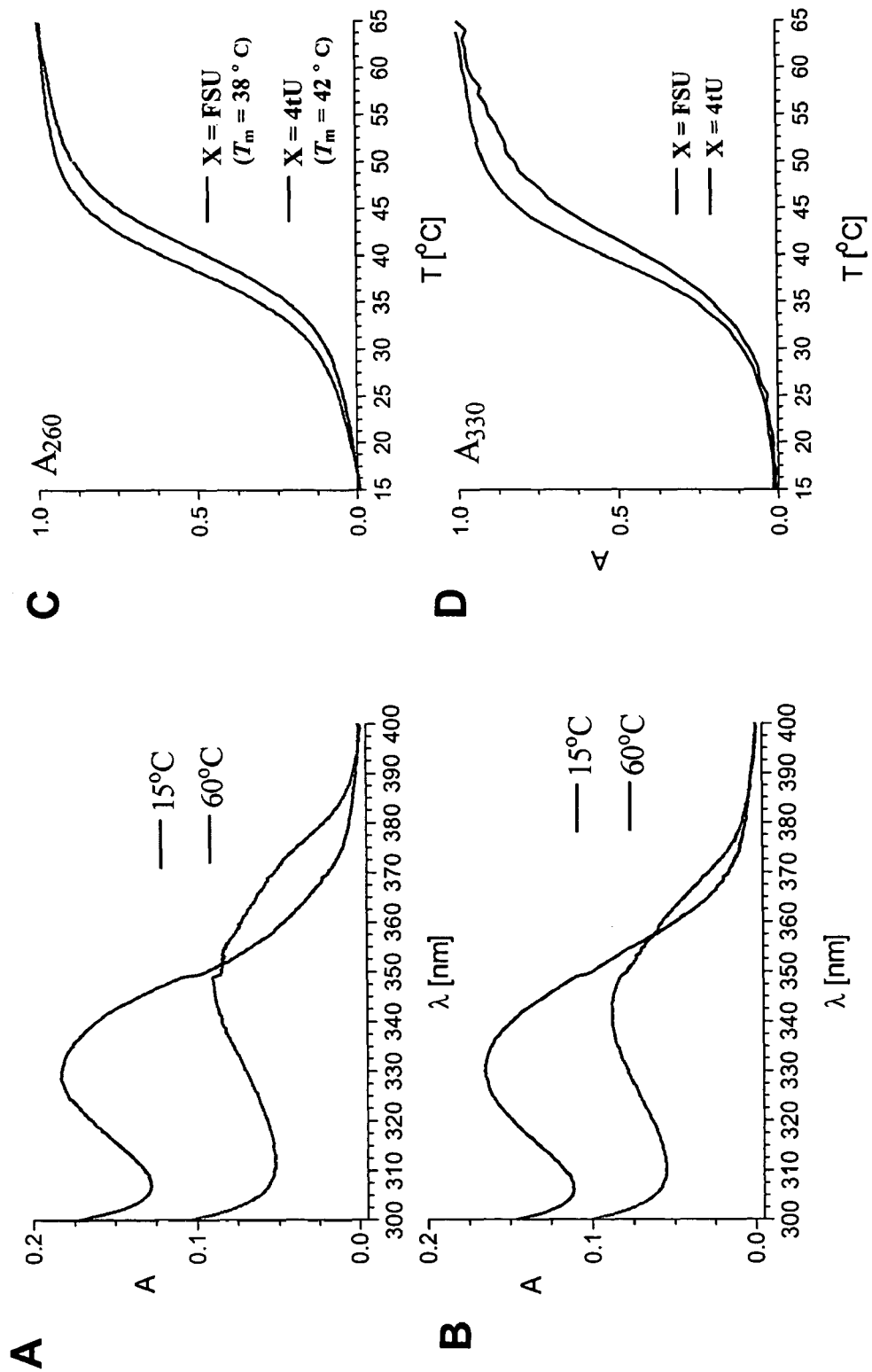
FIG. 7A shows UV absorption spectra for the duplex formed between the dodecamer target sequence, 5'd-TTATCGTATC GT (SEQ ID NO: 1), and the decamer probe sequence, 5'-CGA(FSU)ACGAUA (SEQ ID NO: 4). The darker line showing greater absorption at 330 nm corresponds to the spectra of the hybrid at 60° C., while the other line shows the spectra of the hybrid at 15° C.
FIG. 7B shows UV absorption spectra for the duplex formed between the dodecamer target sequence, 5'd-TTATCGTATC GT (SEQ ID NO: 1), and the decamer control probe sequence, 5'-CGA(4tU)ACGAUA (SEQ ID NO: 5).

FIG. 7C is a graph showing the melting curves for the duplex of the dodecamer target sequence, 5'd-TTATCGTATC GT (SEQ ID NO: 1), and the decamer probe sequence, 5'-CGA(FSU)ACGAUA (SEQ ID NO: 4), and for the duplex of the dodecamer target sequence, 5'd-TTATCGTATC GT (SEQ ID NO: 1), with the decamer control probe, 5'-CGA (4tU)ACGAUA (SEQ ID NO: 5), following absorbance at 260 nm. The melting curve of the duplex containing the probe with the 5-fluoro-4-thiouracil residue (SEQ ID NO: 4) is the left-hand curve. X is the identity of the modified nucleotide (i.e., FSU or 4tU).

FIG. 7D is a graph showing the melting curves for the duplexes described for FIG. 7C, following absorbance at 330 nm. The melting curve of the duplex containing the probe with the 5-fluoro-4-thiouracil residue (SEQ ID NO: 4) is the left-hand curve. X is the identity of the modified nucleotide (i.e., FSU or 4tU).

Figure 8:
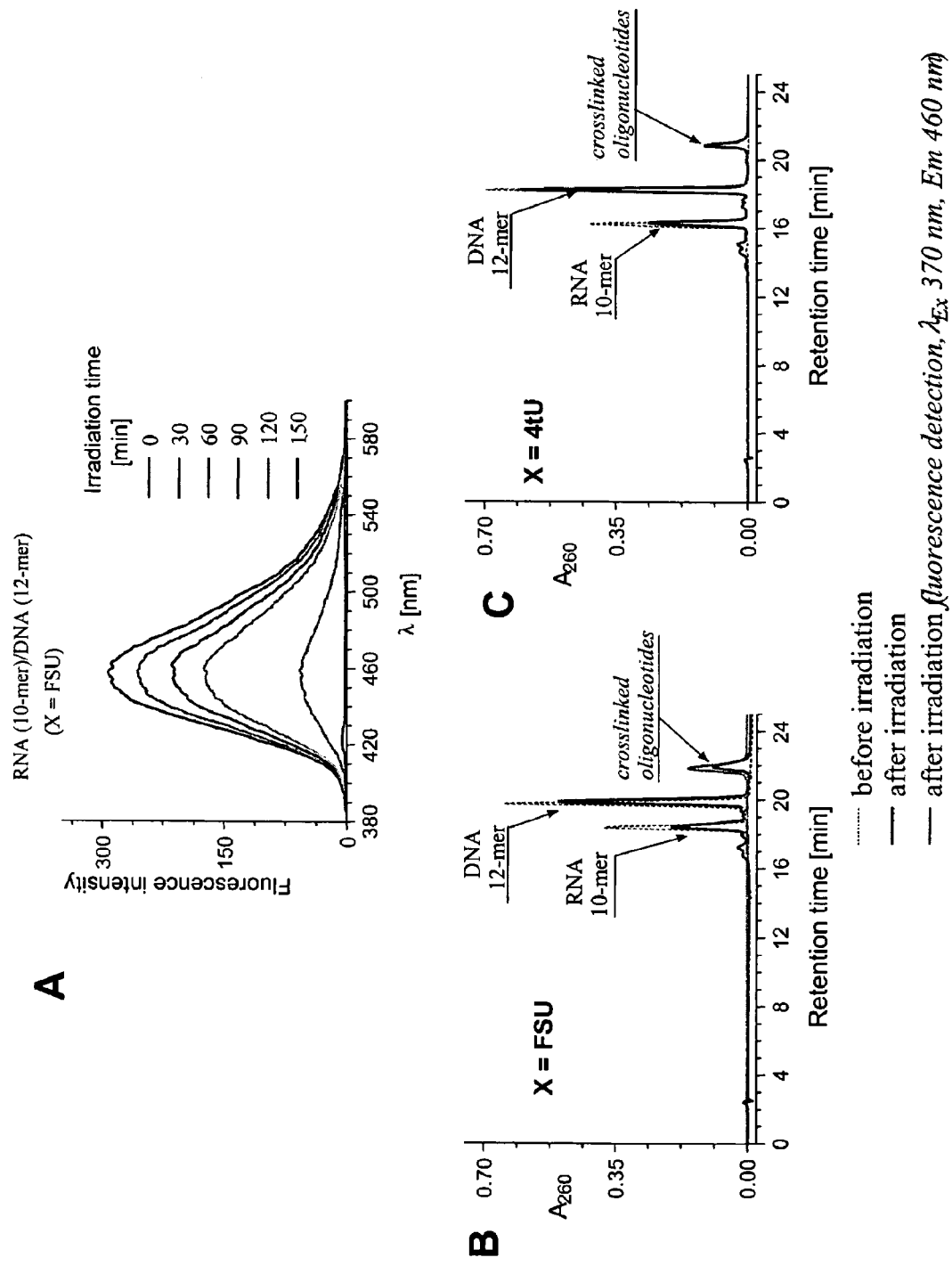

FIG. 8A is a composite of fluorescence emission spectra of the crosslinked product of the hybridized duplex of the dodecamer target sequence, 5'd-TTATCGTATC GT (SEQ ID NO: 1), and the decamer probe sequence, 5'-CGA(FSU)ACGAUA (SEQ ID NO: 4), following irradiation for various time periods, from 0 min to 150 min, as indicated by the legend. X is the identity of the modified nucleotide (i.e., FSU).

FIG. 8B is a composite HPLC chromatogram for the hybridization and irradiation of the duplex described for FIG. 8A. The dotted line is the chromatogram of the mixture prior to irradiation, showing absorbance at 280 nm. The dark solid line is the chromatogram of the mixture after irradiation, again showing absorbance at 280 nm. The lighter solid line is the chromatogram of the mixture after irradiation, measuring fluorescence emission by using an excitation wavelength of 370 nm and observing fluorescence emission at 430 nm. X is the identity of the modified nucleotide (i.e., FSU).

FIG. 8C is a composite HPLC chromatogram for the hybridization and irradiation of the dodecamer target sequence, 5'd-TTATCGTATC GT (SEQ ID NO: 1), and the decamer control probe sequence, 5'-CGA(4tU)ACGAUA (SEQ ID NO: 5). The dotted line shows the chromatogram of the mixture prior to irradiation, measuring absorbance at 280 nm. The dark solid line is the chromatogram of the mixture after irradiation, measuring absorbance at 280 nm. X is the identity of the modified nucleotide (i.e., 4tU).

Figure 9:
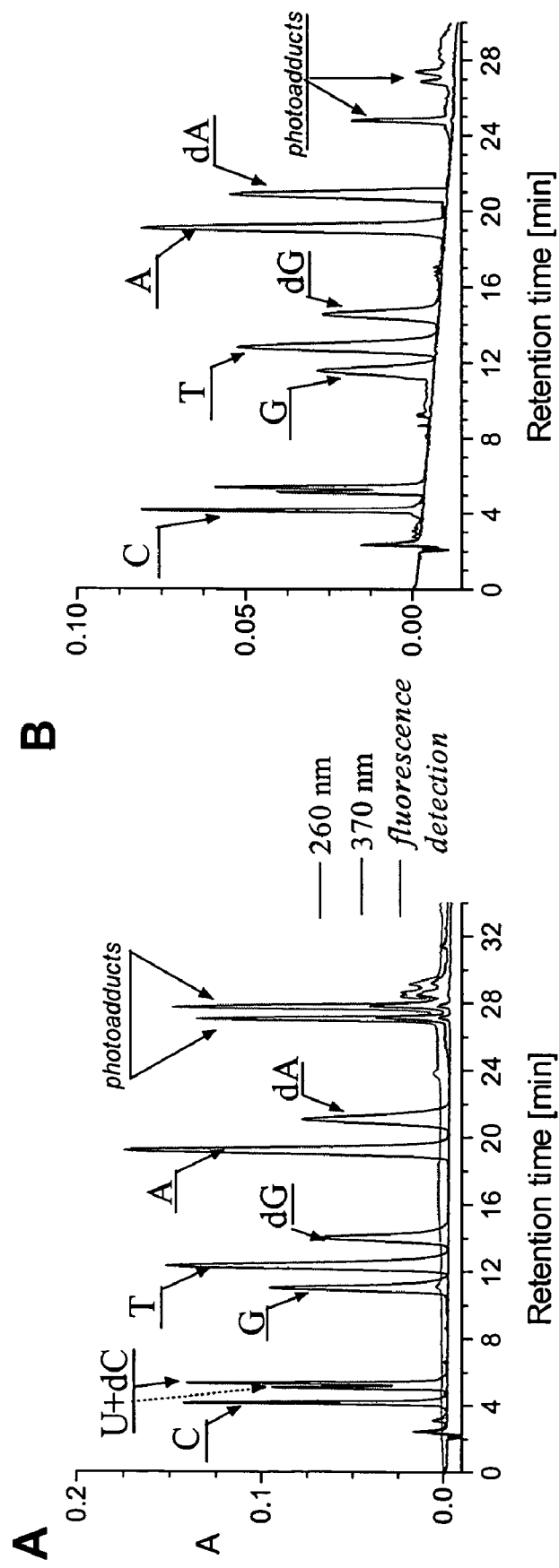

FIG. 9A is a HPLC chromatogram of the enzymatic digestion mixture of the crosslinked duplex of the dodecamer target sequence, 5'd-TTATCGTATC GT (SEQ ID NO: 1), and the decamer probe, 5'-CGA(FSU)ACGAUA (SEQ ID NO: 4). The peaks outlined by the lower heavy solid line (which is mostly flat) were detected at 370 nm. The peaks outlined by the upper heavy solid line were detected at 260 nm. The peaks indicated by the lighter line were detected by observation of fluorescence at 430 nm, following excitation at 370 nm. Peaks attributable to various nucleotides and deoxynucleotides and the peaks attributable to photoadducts are indicated by the arrows and labels.

FIG. 9B is a HPLC chromatogram of the enzymatic digestion mixture of the crosslinked duplex of the dodecamer target sequence, 5'd-TTATCGTATC GT (SEQ ID NO: 1), and the decamer control probe, 5'-CGA(4tU)ACGAUA (SEQ ID NO: 5). The peaks outlined by the lower heavy solid line (which is mostly flat) were detected at 370 nm. The peaks outlined by the upper heavy solid line were detected at 260 nm. Peaks attributable to various nucleotides and deoxynucleotides and the peaks attributable to the photoadducts are indicated by the arrows and labels.

Figure 10:
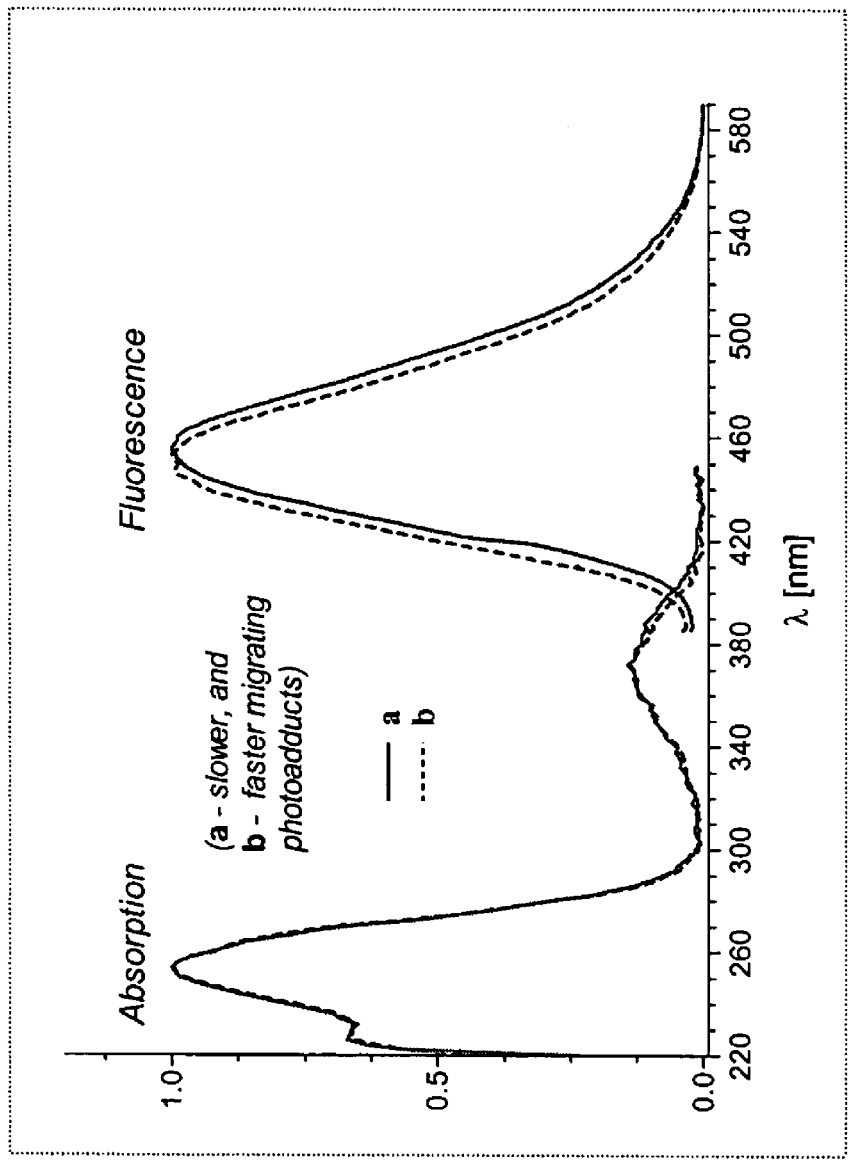

FIG. 10 is a composite of the absorption and fluorescence spectra of the two main photoadducts shown in FIG. 9A. Spectra for the faster migrating (lower retention time) photoadduct, a, is indicated by the solid lines, while those of the slower migrating (longer retention time) photoadduct, b, are shown by dotted lines.

Figure 11:
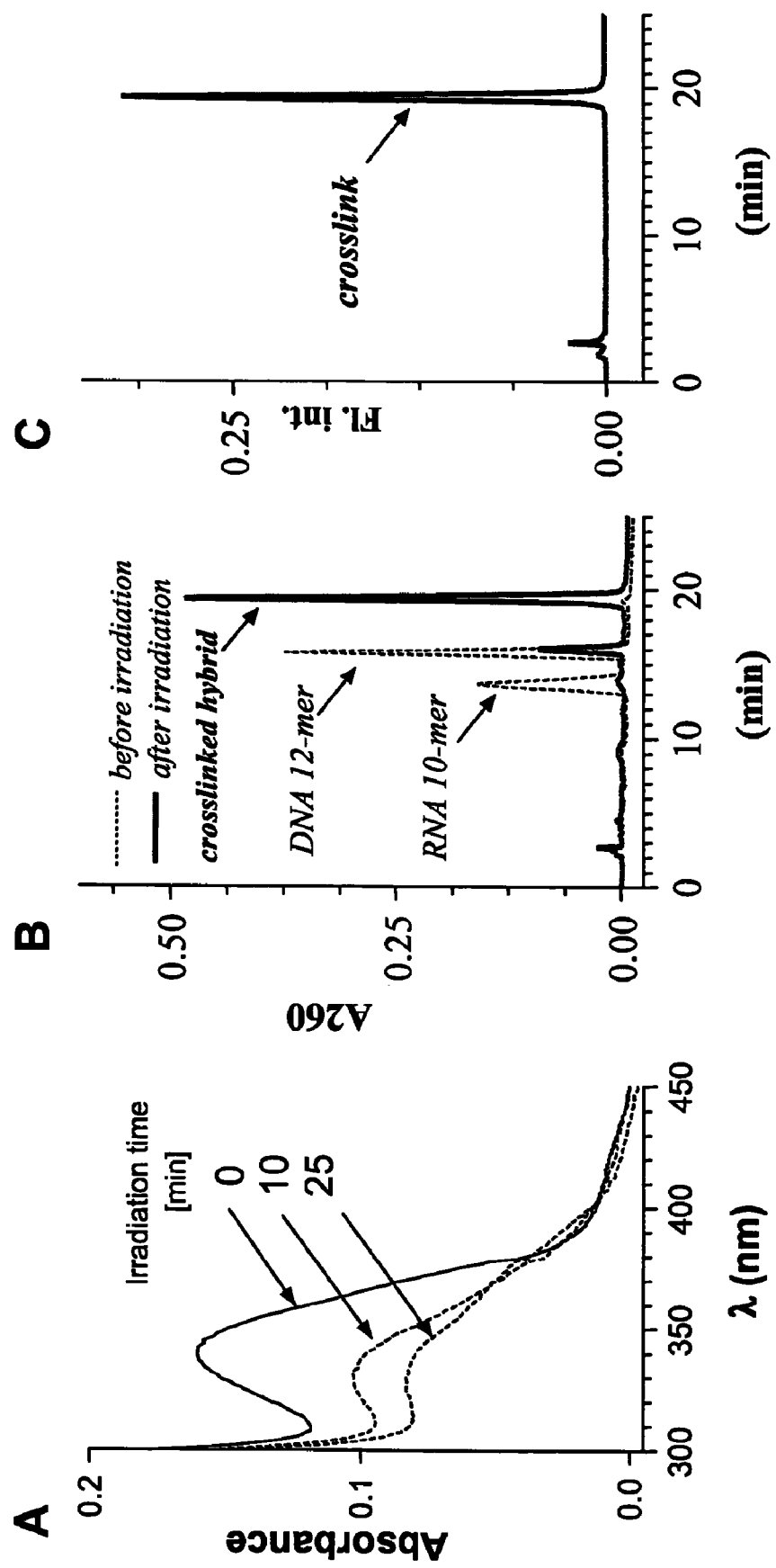

FIG. 11A are absorbance spectra corresponding to the absorbance of the 5-fluoro-4-thiouridine residue during the irradiation of a duplex of the dodecamer target sequence, 5'd-TTATCGTATC GT (SEQ ID NO: 1), and the decamer probe sequence, 5'-CGATACGA(FSU)A (SEQ ID NO: 6). The spectra for duplex irradiated for 0 min, 10 min or 25 min are indicated by the arrows.

FIG. 11B is a composite HPLC chromatogram for the hybridization and irradiation of the duplex described for FIG. 11A. The dotted line shows the absorbance (at 260 nm) of the mixture prior to irradiation. The solid line shows the absorbance (at 260 nm) of the mixture after 25 min of irradiation.

FIG. 11C is a HPLC chromatogram showing the fluorescence intensity of the crosslinked product shown in the chromatogram described in FIG. 11B.

Figure 12:
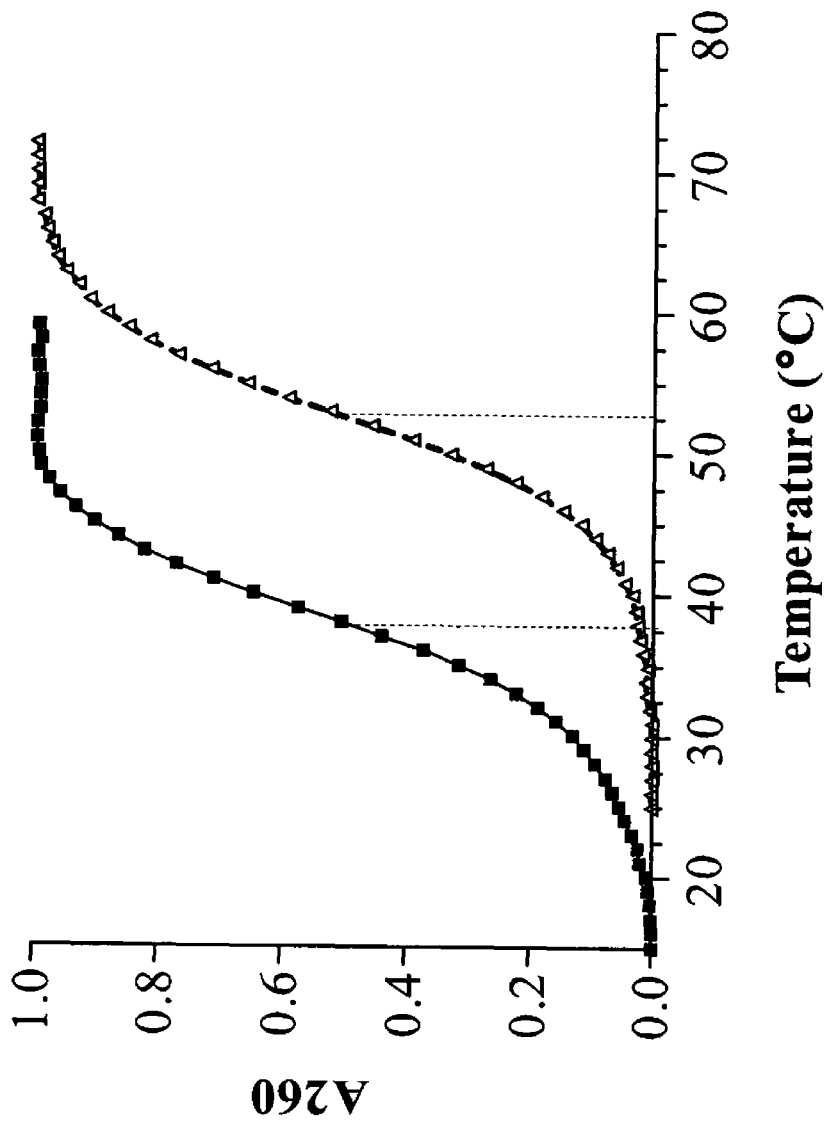

FIG. 12 is a graph comparing the melt curves for the duplex of the dodecamer target sequence, 5'd-TTATCGTATC GT (SEQ ID NO: 1), and the decamer probe sequence, 5'-CGATACGA(FSU)A (SEQ ID NO: 6), both before (dark squares) and after (open triangles) irradiation and formation of the photocrosslink.

Figure 13:
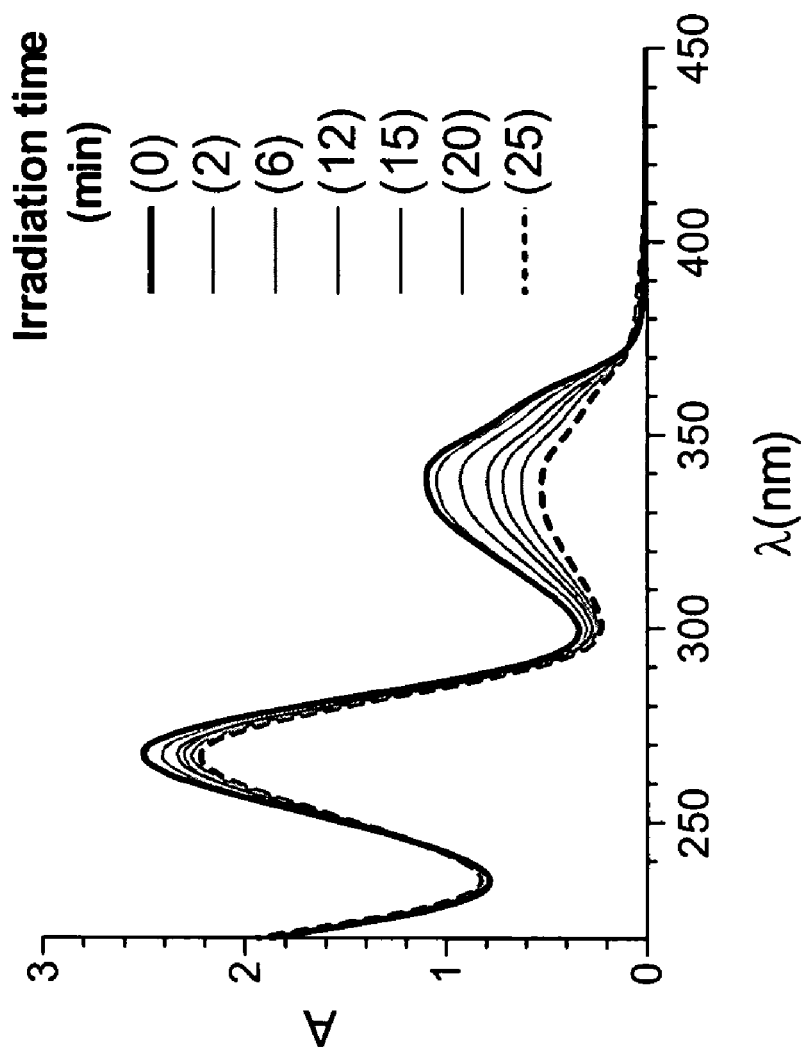

FIG. 13 is UV absorption spectra of the reaction mixture of 5-fluoro-4-thiouridine and thymidine after irradiation at various times, from 0 minutes to 25 minutes as shown in the legend. The absorbance intensity decreases over time.

Figure 14:
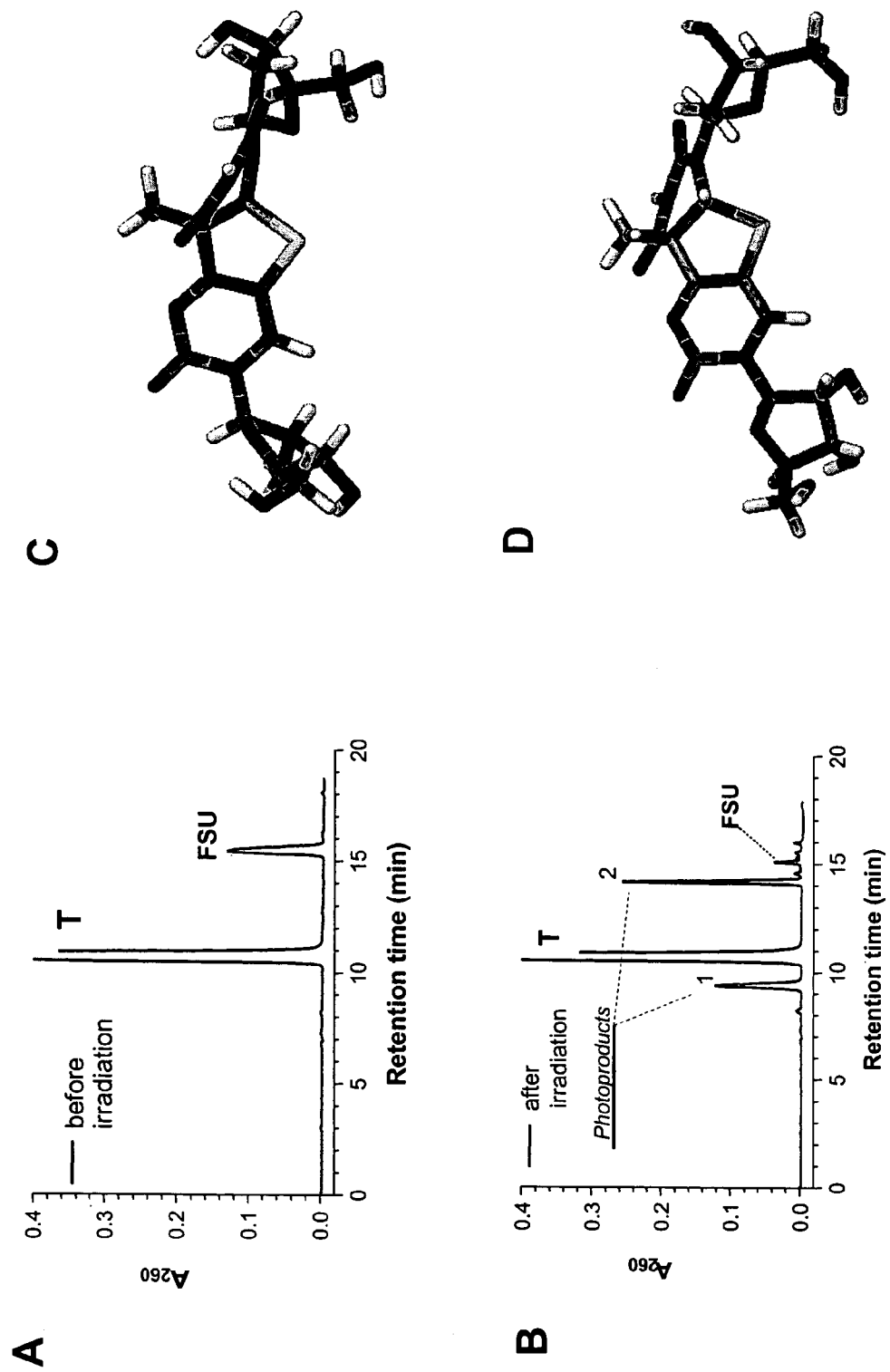

FIG. 14A is a HPLC chromatogram of the reaction mixture of 5-fluoro-4-thiouridine (FSU) and thymidine (T) in solution prior to irradiation, measuring absorbance at 260 nm.

FIG. 14B is a HPLC chromatogram of the reaction mixture of 5-fluoro-4-thiouridine (FSU) and thymidine (T) in solution following irradiation at 366 nm for 25 min, then measuring absorbance at 260 nm.

FIG. 14C is a drawing of one possible isomeric structure of the photoadduct of 5-fluoro-4-thiouridine and thymidine.

FIG. 14D is a drawing of a second possible isomeric structure of the photoadduct of 5-fluoro-4-thiouridine and thymidine.

Figure 15:
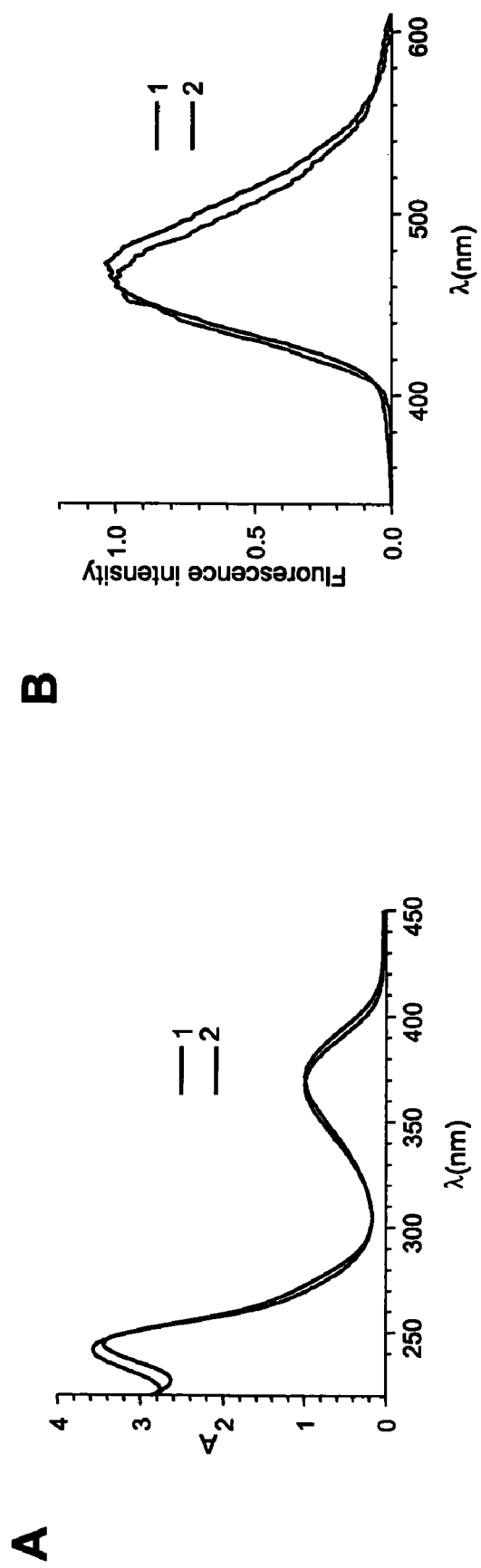

FIG. 15A is UV absorption spectra of the two photoproducts, 1 and 2, shown in FIG. 14B. The spectrum for 2 is slightly to the left of that for 1. The absorption maxima of photoproduct 1 are at 244 nm and 372 nm, while those of photoproduct 2 are at 242 nm and 367 nm.

FIG. 15B is fluorescence spectra of the two photoproducts, 1 and 2, shown in FIG. 14B. The spectrum for 2 is slightly to the left of that for 1. The maximum fluorescence emission for photoproduct 1 is at 470 nm, while the maximum fluorescence emission for photoproduct 2 is at 460 nm.

Figure 16A:
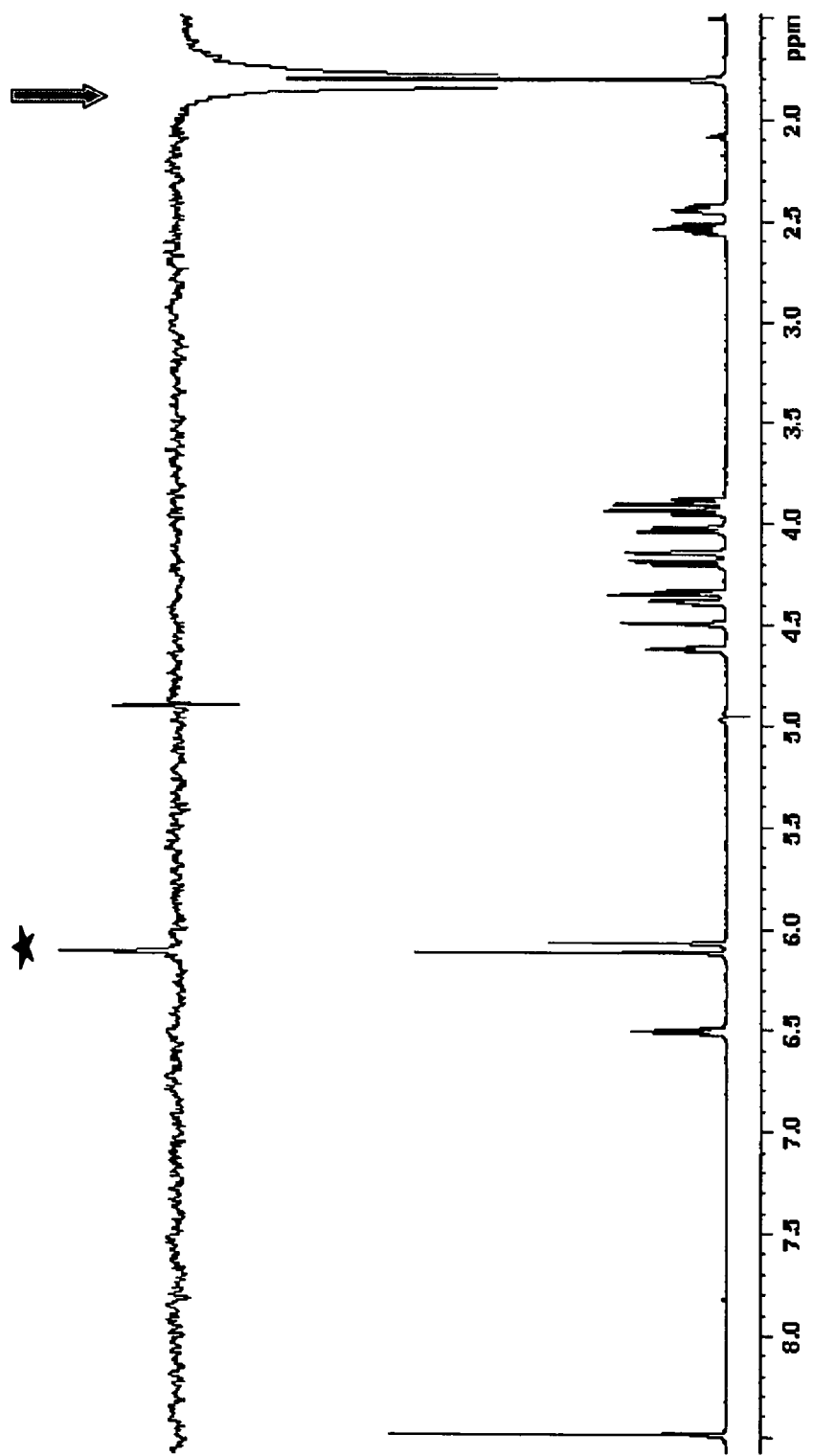

FIG. 16A shows a one-dimensional (1-D) NOE NMR spectrum of photoproduct 1.

Figure 16B:
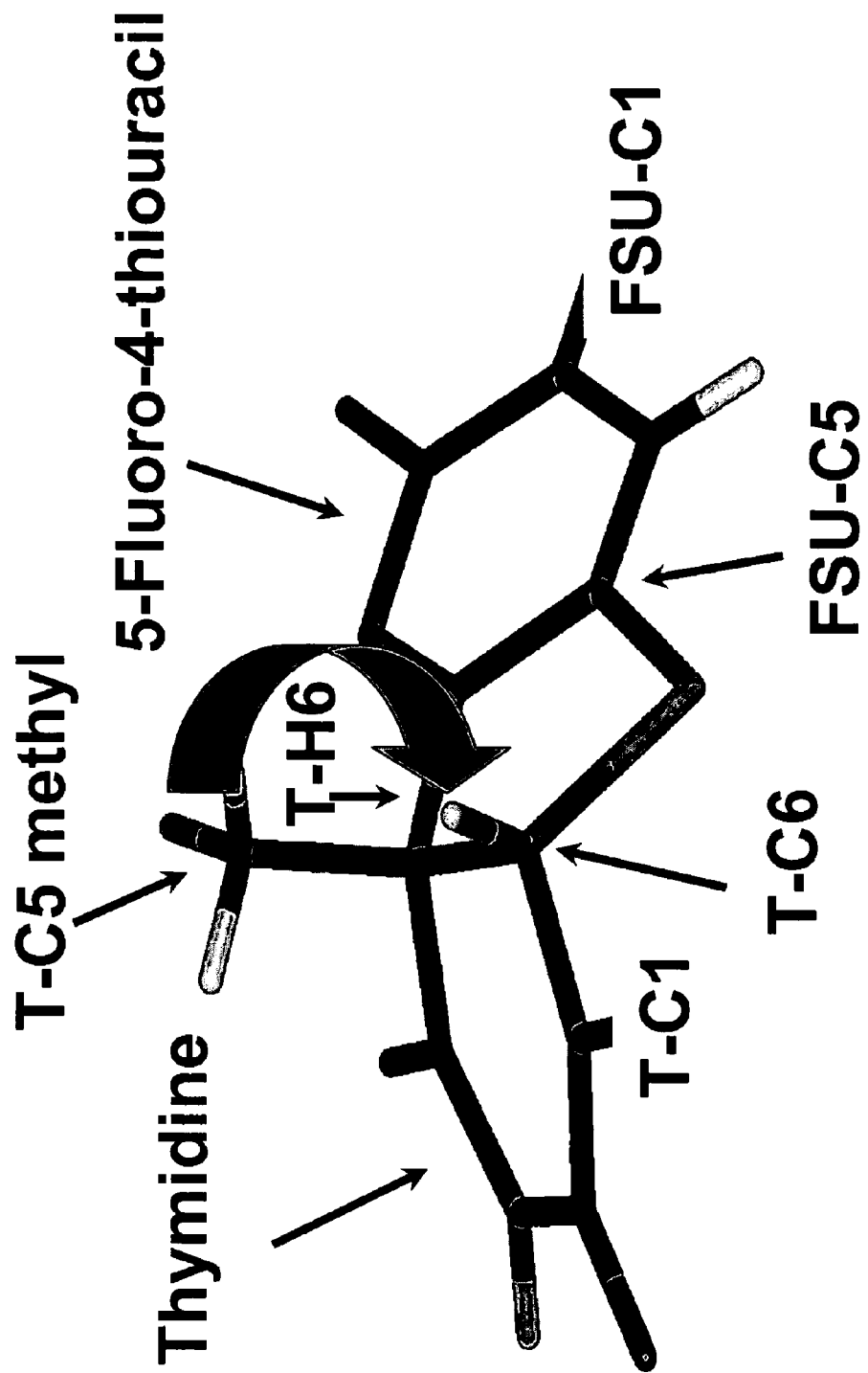

FIG. 16B is a schematic drawing of photoproduct 1 showing the stereochemistry of the methyl group. The NOE interaction that defines the spatial relationship between the thymidine C5 (T-C5) methyl group and the thymidine H6 (T-H6) hydrogen atom on the adjacent carbon is indicated by the arrow in FIG. 16B.

Figure 17:
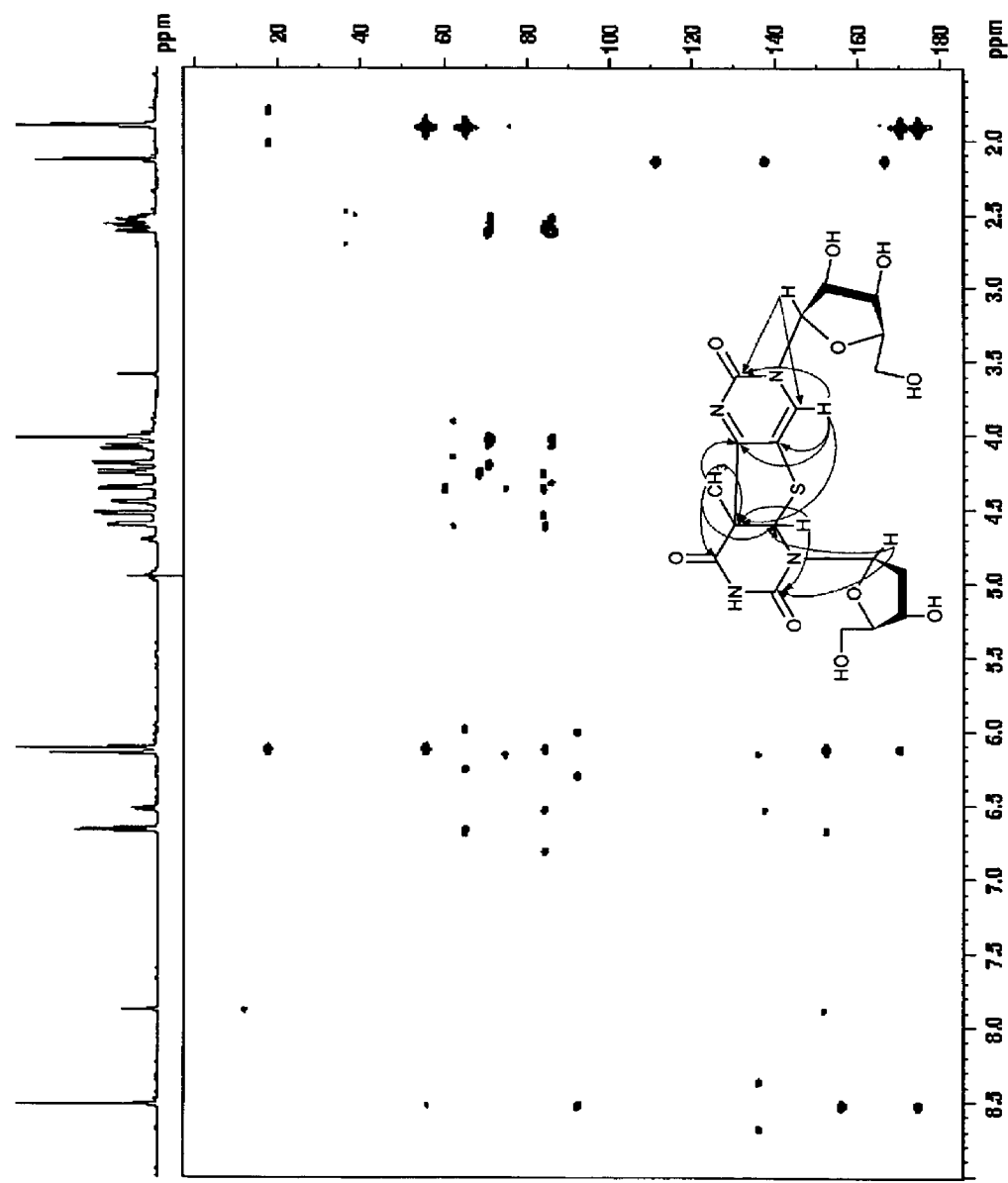

FIG. 17 is a two-dimensional (2-D) $^1$H-$^{13}$C HMBC NMR spectrum of one of the two photoproducts from the photoreaction of 5-fluoro-4-thiouridine and thymidine.

Figure 18:
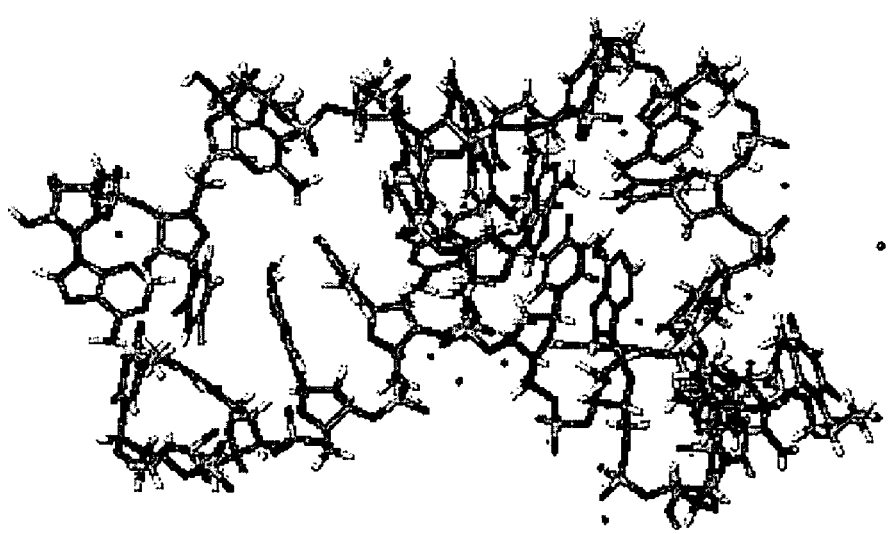

FIG. 18 is a schematic drawing showing the structures obtained from (constrained) energy minimization of the DNA/RNA oligonucleotide duplex of the dodecamer target sequence, 5'd-TTATCGTATC GT (SEQ ID NO: 1), and the decamer probe sequence, 5'-CGA(FSU)ACGAUA (SEQ ID NO: 4), showing the initial approach of the 5-fluoro-4-thiouridine in the RNA (SEQ ID NO: 4) and the thymidine at the second position in the DNA sequence (SEQ ID NO: 1).

Figure 19:
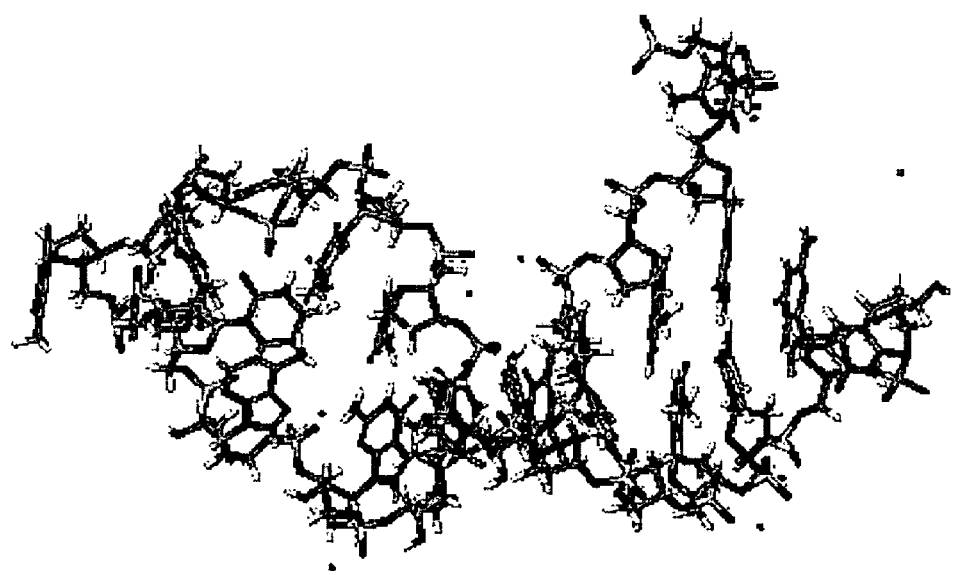

FIG. 19 is a schematic drawing showing the structures obtained from (constrained) energy minimization of the DNA/RNA oligonucleotide duplex of the dodecamer target sequence, 5'd-TTATCGTATC GT (SEQ ID NO: 1), and the decamer probe sequence, 5'-CGA(FSU)ACGAUA (SEQ ID NO: 4), showing the initial approach of the 5-fluoro-4-thiouridine in the RNA sequence (SEQ ID NO: 4) and the thymidine at the fourth position in the DNA sequence (SEQ ID NO: 1).

Figure 20:
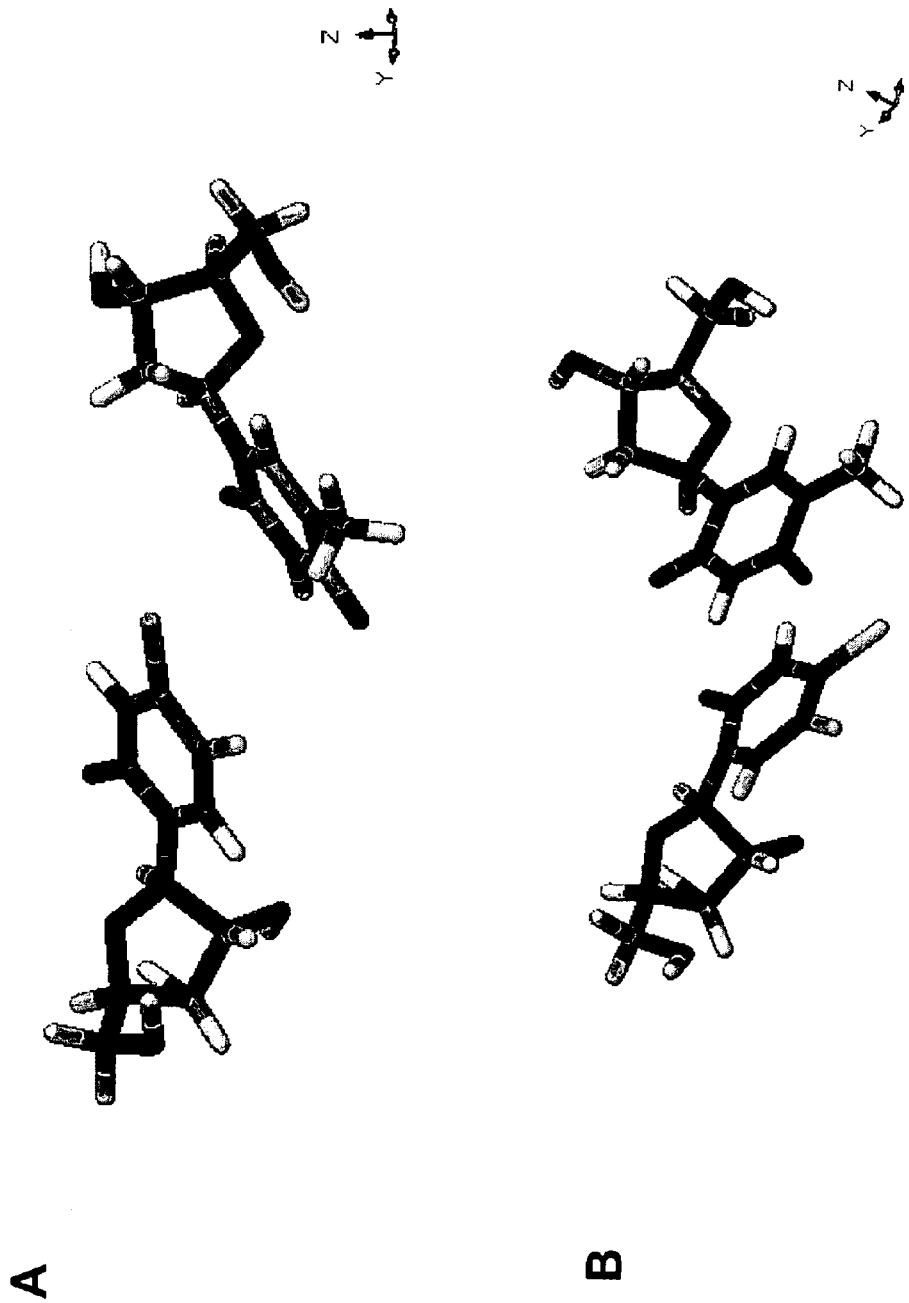

FIG. 20A is a schematic drawing showing the energy minimized excised structures of the two interacting nucleotides (5-fluoro-4-thiouridine and thymidine 2) using density functional theory (DFT) methods. The two bases were obtained from the geometry of the complete oligonucleotide shown in FIG. 18, wherein the phosphodiester bonds to neighboring nucleotides were removed and the oxygen atoms capped with hydrogen atoms.

FIG. 20B is a schematic drawing showing the energy minimized excised structures of the two interacting nucleotides (5-fluoro-4-thiouridine and thymidine 4) using density functional theory (DFT) methods. The two bases were obtained from the geometry of the complete oligonucleotide shown in FIG. 19, wherein the phosphodiester bonds to neighboring nucleotides were removed and the oxygen atoms capped with hydrogen atoms.

Figure 21:
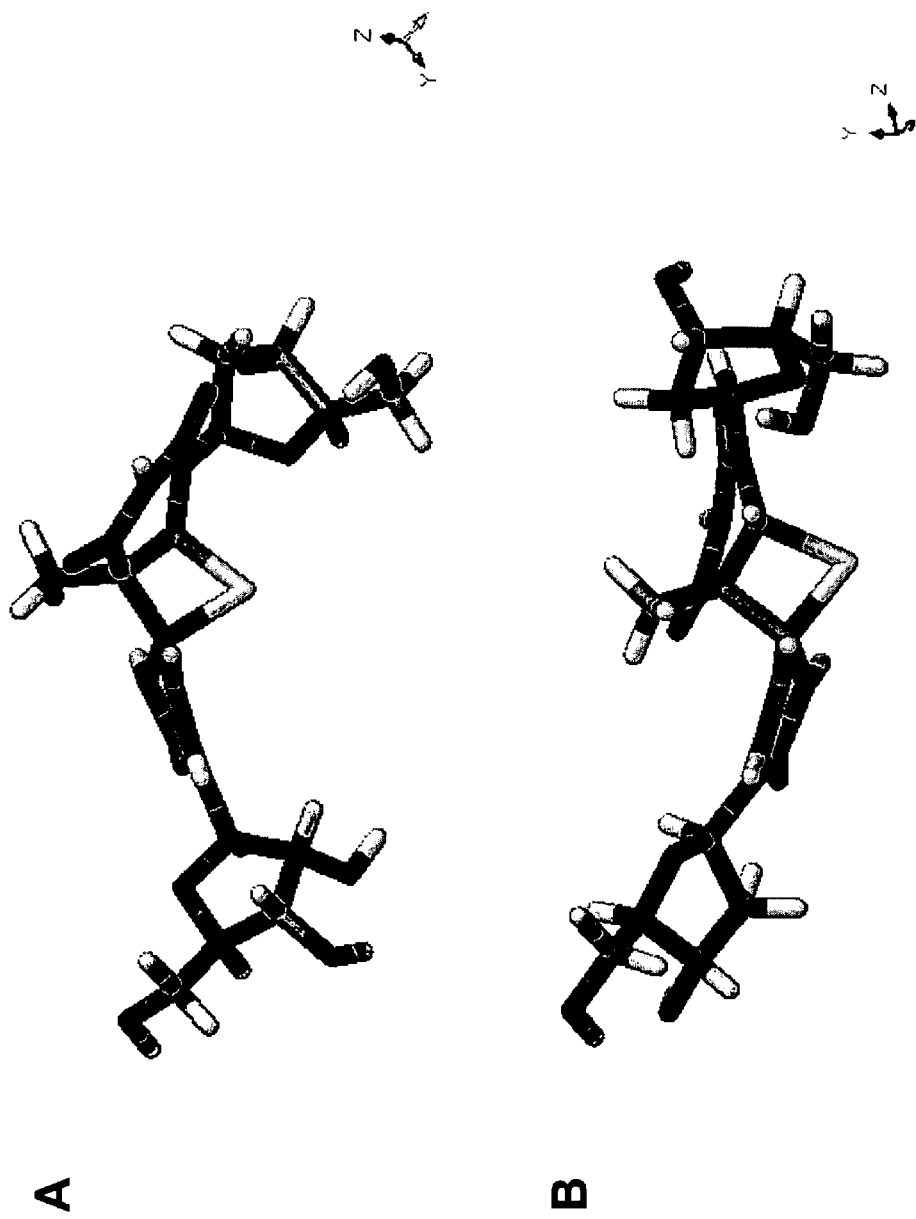

FIG. 21A is a schematic drawing showing the energy minimized excised structure of the pseudo-cyclobutane intermediate D2_I formed upon the initial photoreaction of 5-fluoro-4-thiouridine with thymidine at position 2.

FIG. 21B is a schematic drawing showing the energy minimized excised structure of the pseudo-cyclobutane intermediate D4_I formed upon the initial photoreaction of 5-fluoro-4-thiouridine with the thymidine at position 4.

Figure 22:
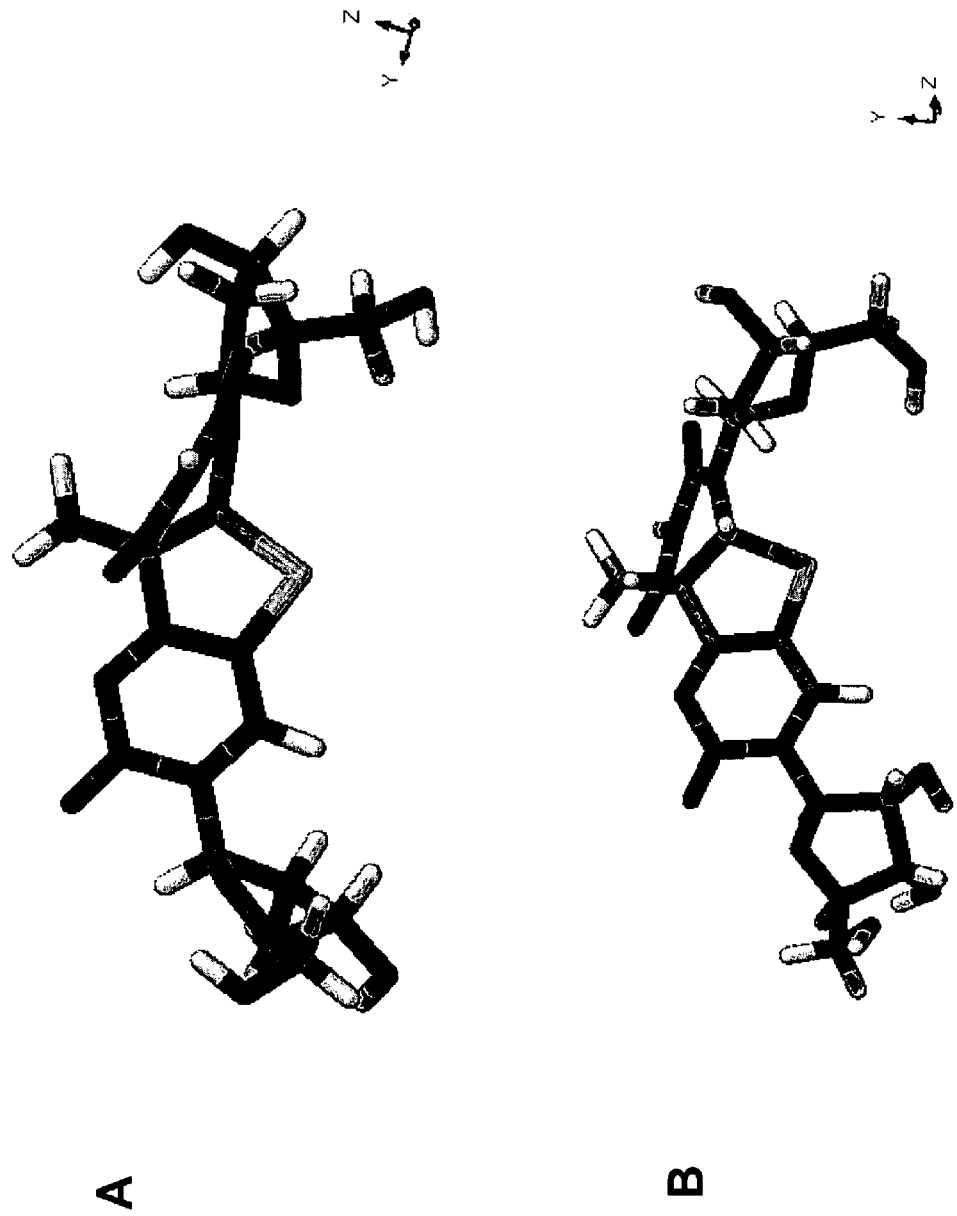

FIG. 22A is a schematic drawing showing the energy minimized excised structure of the final photoadduct D2_F.

FIG. 22B is a schematic drawing showing the energy minimized excised structure of the final photoadduct D4_F.

Figure 23:
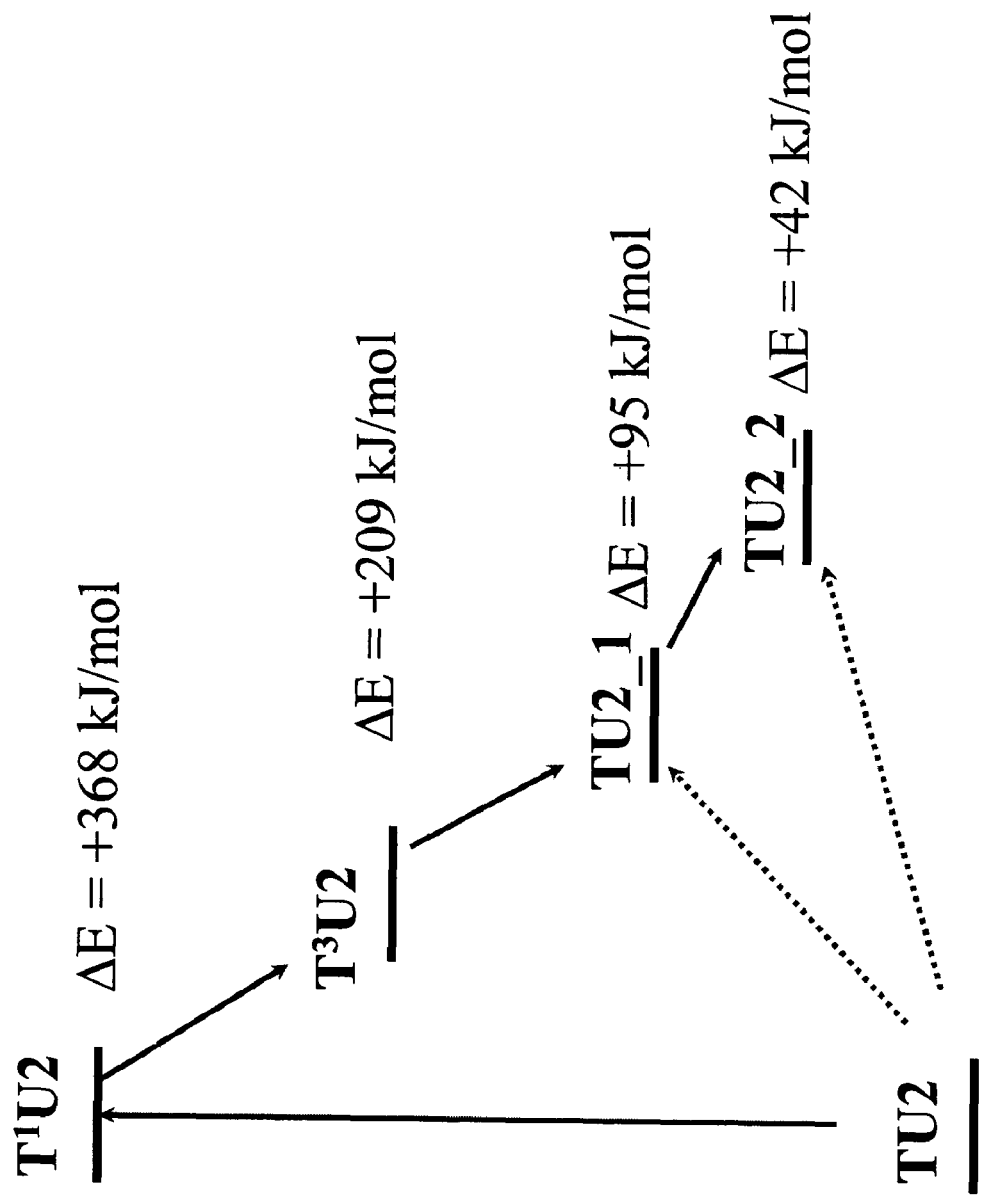

FIG. 23 is a schematic showing an energy diagram calculated by DFT methods for the photoreaction of the RNA molecule, 5'-CGA(FSU)ACGAUA (SEQ ID NO: 4), and the thymidine at position 2 in the dodecamer target DNA sequence, 5'd-TTATCGTATC GT (SEQ ID NO: 1). TU2 refers to the ground state of the 5-fluoro-4-thiouridine, $T^1U2$ refers to the excited singlet state, $T^3U2$ refers to the excited triplet state, TU2_I refers to the pseudo-cyclobutane intermediate, and TU2_2 to the final photoadduct.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

Following long-standing patent law convention, the terms "a", "an", and "the" refer to "one or more" when used in this application, including the claims. Thus, for example, reference to "a cell" includes mixtures of one or more cells, two or more cells, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, time, dose, etc. is meant to encompass in one example variations of ±20% or ±10%, in another example ±5%, in another example ±1%, and in yet another example ±0.1% from the specified amount, as such variations are appropriate to perform the disclosed methods.

As used herein the term "alkyl" refers to $C_{1-20}$ inclusive, linear (i.e., "straight-chain"), branched, or cyclic (a "cycloalkyl"), saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls. In some embodiments, alkyl is a $C_1$-$C_5$ (e.g., 1, 2, 3, 4, or 5 carbon atoms) linear or branched alkyl group.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Further, as used herein, the terms alkyl and/or "substituted alkyl" include an "allyl" or an "allylic group." The terms "allylic group" or "allyl" refer to the group —CH$_2$HC=CH$_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic."

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R', wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, fluorene, and the like.

In some embodiments, the compounds described by the presently disclosed subject matter contain a linking group or a spacer group. As used herein, the terms "linking group" and "spacer group" comprises a chemical moiety, alkylene or arylene group, which is bonded or can be bonded to two or more other chemical moieties, in particular to nucleic acids and solid support materials. The linking or spacer group can include reactive chemical moieties at each end, which can react to form covalent bond with the molecules or groups being linked.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_1$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

As used herein, the term "acyl" refers to an organic carboxylic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Acylamino" refers to an acyl-NH— group wherein acyl is as previously described.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

The terms "halo", "halide", or "halogen" as used herein refer to fluoro, chloro, bromo, and iodo groups.

The term "amino" refers to the —NH$_2$ group. The term "secondary amino group" refers to an amino group wherein the two hydrogen atoms are replaced by alkyl or aryl groups. The alkyl groups can be linear, branched or cyclic. The alkyl groups may include one or more heteroatoms in place of a carbon in the alkyl chain. Further, the two alkyl groups can together form an alkylene group or an alkylene group containing one or more heteroatoms.

The terms "oxy" and "ether" refer to an —O— group.

The terms "thio" and "mercapto" refer to a compound described previously herein wherein a carbon or oxygen atom is replaced by a sulfur atom.

The term "cyano" refers to a carbon radical triple bonded to a nitrogen atom. A cyano group can be represented as —CN.

The term "nitro" refers to the —NO$_2$ group.

The terms "carboxy" or "carboxyl" refer to the —COOH group.

The term "carbonyl" refers to the —(C=O)— group.

The term "thiocarbonyl" refers to the —C(=S)— group.

The terms "alkylsulfonyl" and "arylsulfonyl" refer to the —OS(O)$_2$-alkyl and —O—S(O)$_2$-aryl groups respectively, wherein alkyl and aryl are as defined herein above.

The term "silyl ether" refers to a O—Si—(R)$_3$ group. The silyl ether can comprise a trialkylsilyl group (i.e., a —Si(R)$_3$ group wherein each of the R groups is independently a linear or branched alkyl). Alternatively, one or more of the R substituents can be aryl or substituted aryl (i.e., a methoxyphenyl group).

The term "trityl" refers to the triphenylmethyl ether group.

When the term "independently selected" is used, the substituents being referred to (e.g., R groups, such as groups $R_1$ and $R_2$, or groups $X_1$ and Y), can be identical or different.

A dashed line representing a bond indicates that the bond can be present or absent. For example, a structure such as:

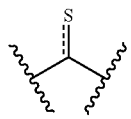

represents a structure comprising a carbon-sulfur single bond or a carbon-sulfur double bond.

Wavy lines are used in the chemical formulas described herein to indicate the attachment site of the specified structure to another chemical group, for example, to a nucleoside sugar or to the backbone of a nucleic acid or oligonucleotide.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar properties as the reference nucleic acid and are metabolized in a manner similar to naturally occurring nucleotides. Nucleic acids can be derived from a variety of sources including, but not limited to, naturally occurring nucleic acids, clones, or chemically synthesized (either in solution or by solid phase synthesis) nucleic acids. Nucleic acid polymers can have any number of nucleotides.

The term "nucleotide" refers to the monomer unit of a nucleic acid or oligonucleotide polymer. A nucleotide typically comprises a nucleobase attached to a sugar-phosphate backbone moiety. In naturally occurring nucleotide polymers, the sugar-phosphate backbone moiety generally comprises phosphodiester linkages and a pentose sugar. In some embodiments, the term "nucleotide" refers to a nucleotide residue, i.e., one particular monomer in an oligonucleotide or nucleic acid polymer.

The term "nucelobase" can include natural heterocyclic bases, such as adenine (A), guanine (G), cytosine (C), uracil (U), or thymine (T), inosine, 5-methylcytosine, xanthine, and hypoxanthine, or can be a non-naturally occurring nucleobase or nucleobase analogue, such as, but not limited to, azaadenine, azacytosine, azaguanine, 5-bromo-uracil, thiouracil, bromothymine, 7,8-dimethyl alloxazine, and 2,6-diaminopurine.

The term "nucleoside" refers to a nucleobase attached to a sugar moiety.

The term "protected sugar moiety" refers to a sugar, such as, but not limited to ribose and deoxyribose, wherein each of the hydroxyl groups is capped by a suitable hydroxyl protecting group. Any suitable hydroxyl protecting group known in the art of synthetic organic chemistry and/or nucleic acid synthesis can be used. Some useful hydroxyl protecting groups include, but are not limited to, acyl groups, methoxymethyl ethers, benzyl ethers, trityl ethers, substituted trityl ethers (i.e., containing one or more substituted phenyl groups), and silyl ethers. Other hydroxyl protecting groups can be used, as described further hereinbelow. Numerous additional hydroxyl protecting groups are disclosed in "Protective Groups in Organic Synthesis," Greene, T. W., and P. G. M. Wuts, eds., 3$^{rd}$ Ed., Wiley-Interscience, New York, 1999.

In some embodiments, multiple hydroxyl groups in the sugar are protected by the same protecting group or by protecting groups that can be removed using the same reagents. In some embodiments, each of the hydroxyl groups are protected by a different protecting group, allowing for selective deprotection of each hydroxyl group. In some embodiments, the hydroxyl protecting groups are compatible with the conditions used in solid phase oligonucleotide synthesis, for example, using phosphoramidite methodology.

The term "partially protected sugar" refers to a sugar having at least one hydroxyl group unprotected (i.e., present as an —OH moiety) and at least one hydroxyl group protected by a suitable hydroxyl protecting group.

As used herein "oligonucleotide" refers to a polymer comprising ribonucleotide and/or deoxyribonucleotide residues. Generally, an oligonucelotide will comprise between 2 and 500 nucleotide residues. One end of an oligonucleotide or nucleic acid polymer can be referred to as the 5' end. The 5' end is the end having a terminal phosphate bonded to the C-5 carbon of the pentose sugar. The other end is the 3' end.

The term "complementary" refers to two oligonucleotide sequences that comprise antiparallel nucleotide sequences capable of pairing with one another upon formation of hydrogen bonds between the complementary base residues in the antiparallel nucleotide sequences. As is known in the art, the nucleic acid sequences of two complementary strands are the reverse complement of each other when each is viewed in the 5' to 3' direction.

The term "hybridization" refers to the process in which two single-stranded oligonucleotides bind non-covalently to form a stable double-stranded oligonucleotide. The resulting double-stranded oligonucleotide is a "hybridized duplex," or more simply, a "hybrid" or "duplex." Triple-stranded hybridization is also possible. Double-stranded hybrids can contain two DNA strands, two RNA strands, or one DNA strand and one RNA strand.

As is also known in the art, two sequences that hybridize to each other under a given set of conditions do not necessarily have to be 100% fully complementary. The terms "fully complementary" and "100% complementary" refer to sequences for which the complementary regions are 100% in Watson-Crick base-pairing, i.e., that no mismatches occur within the complementary regions. However, certain of these molecules can have non-complementary overhangs on either the 5' or 3' ends.

The term "essentially complementary" refers to sequences that, under particular hybridization conditions, preferentially or exclusively hybridize to one another, as opposed to hybridizing with any other oligonucleotide or nucleic acid sequence present.

The terms "crosslink", "crosslinkage", and grammatical derivatives thereof refer to the interstrand covalent bonding or bonds between two oligonucleotides or nucleic acid sequences.

The term "photocrosslink" and its grammatical derivatives refer to a crosslink whose formation is catalyzed by light. The light can be of visible or nonvisible wavelengths. In some embodiments, the light is UV light.

As used herein a "probe" is defined as an oligonucleotide capable of binding to a target nucleic acid of complementary sequence through one or more types of chemical bonds, usually through complementary base pairing.

As used herein, a probe can include natural bases (i.e. A, G, U, C, or T) or analogs, modified or unusual bases whether synthetic or naturally occurring (7-deazaguanosine, inosine, etc.). For example, the probe can contain one or more 5-halo-4-thiouracil. In addition, the monomeric units in probes can be joined by a linkage other than a phosphodiester bond. Any portion of nucleic acids can be other than that found in nature. Thus, probes can be peptide nucleic acids in which the constituent bases are joined by peptide bonds rather than phosphodiester linkages. It is also envisioned that the definition of probes can include mixed nucleic acid peptide probes.

The term "target nucleic acid" or "target sequence" refers to a nucleic acid or nucleic acid sequence that is to be analyzed. A target can be a nucleic acid to which a probe can hybridize. The probe can be specifically designed to hybridize to the target. It can be either the presence or absence of the target nucleic acid that is to be detected, or the amount of the target nucleic acid that is to be quantified. The term target nucleic acid can refer to the specific subsequence of a larger nucleic acid to which the probe is directed or to the overall sequence (e.g., the gene or mRNA) whose expression level it is desired to detect. The difference in usage will be apparent from context.

The term "cDNA" as used herein means a complementary DNA molecule made as a copy of mRNA amplified using PCR. cDNAs can range from about 100 bp to about 8,000 bp, where average cDNAs are typically 1 to 2 kb in length. CDNA can also refer to a complementary DNA molecule made as a copy of mRNA using reverse transcriptase and be a single or double stranded molecule An "array" represents an intentionally created collection of molecules which can be prepared either synthetically or biosynthetically. In particular, the term "array" means an intentionally created collection of oligonucleotides attached to at least a first surface of at least one solid support. In some embodiments, each molecule of the array is attached at a discrete region of the solid support. In some embodiments, the identity (i.e., the nucleotide sequence) of the oligonucleotide attached at each descrete region of the support is known. The terms "array", "biological chip", "DNA chip" and "chip" are used interchangeably.

A "discrete, known location," "array address," or "address" refer to a localized area on a solid support which is intended to be used for the formation or attachement of a particular molecule or group of molecules (i.e., one specific probe or group of probes).

The term "fluorophore" refers to a molecule or to a chemical moiety within a molecule that emits light following exposure to radiant energy, such as electromagnetic radiation. In particular, a fluorophore is a group that emits visible light after exposure to electromagnetic radiation. The electromagnetic radiation can be, for example, UV light.

II. Modified Nucleobase Probes

II.A. Modified Uracils

Photocrosslinking groups include modified uracil nucleobases, such as 4-thiouridine and the 5-halouridines. The structures of nucleosides containing these modified uracils are shown below in Scheme 1.

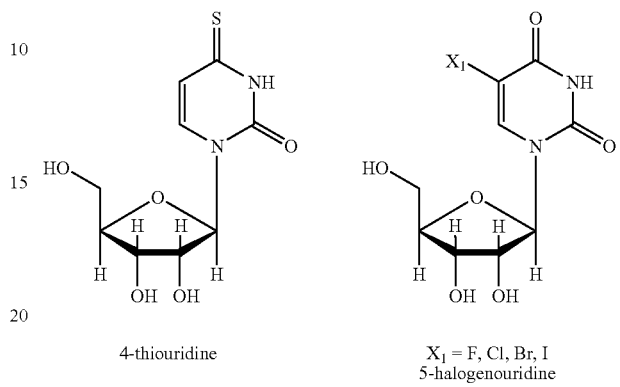

4-thiouridine $X_1$ = F, Cl, Br, I
5-halogenouridine

Scheme 1. Nucleosides with modified uracil bases.

4-Thiouridine is a rare, naturally occurring nucleoside discovered in 1965 in *E. coli* tRNA. See Lipsett, M. N., *J. Biol. Chem.*, 240, 3975-3978 (1965). Due to the presence of the sulfur atom in place of the oxygen in the carbonyl group at position 4, the UV absorption of 4-thiouridine is red shifted to approximately 330 nm. Thus, 4-thiouridine can be selectively photoactivated, because all the usual components of RNA and DNA have absorption maxima below 300 nm.

4-Thiouridine and similar groups, such as 4-thiothymidine and 4-thiodeoxyuridine can be incorporated into the oligonucleotide sequences of RNAs and DNAs with little structural perturbation. When photoexcited, 4-thiouridine reacts with uracil and cytosine to yield photoadducts. Probes containing thiouracil have been used in many studies to determine the folding of ribozymes and the nature of RNA-protein interactions in spliceosomes and polymerases. See Favre, A., et al., *J. Photochem. Photobiol*. B, 42, 109-124 (1998).

The 5-halouracils can also be selectively photoexcited and have been successfully introduced into RNA or DNA for use in crosslinking studies with proteins. Upon irradiation at 325 nm, 5-iodouracil forms adducts with tyrosine and phenylalanine derivatives by covalent linkage between carbon five of the nucleobase and a carbon on the aromatic ring of the amino acid residue. Model studies of the reactions of 5-bromouracil have demonstrated cross-linking to tyrosine, histidine, tryptophan, and cysteine after irradiation at 308 nm. See Norris, C. L., et al., *J. Am. Chem. Soc.*, 118, 5796-5803 (1996).

II.B. 5-Halo-4-Thiouracils

The synthesis, spectral, and photophysical properties of 5-halo-4-thiouridines derivatives have recently been reported. See Wenska, G., et al., *J. Chem. Soc., Perkin Trans.* 1, 53-57 (2002); Taras-Goślińska, K., et al., *J. Photochem. Photobiol. A,* 168, 227-233 (2004); and Wenska, G., et al., *J. Org. Chem.,* 70, 982-988 (2005). In particular, studies of the 2', 3', 5'-tri-O-acetyl-5-halo-4-thiouridines reveal that, like thiouracil, the 5-halo-4-thiouridines have UV absorption spectra with absorption maxima of approximately 330 nm in $CCl_4$. See, Taras-Goślińska, K., et al., *J. Photochem. Photobiol. A,* 168, 227-233 (2004). In water at physiological pH, the absorption maxima of the neutral forms of the tri-O-acetyl-5-halo-4-thiouridines are approximately 340 nm, while that of the anions are 327 nm.

Studies of the photochemical reactions of 5-halo-4-thiouridines suggest that homolysis of the carbon-halogen bond is the primary photochemical step; however, the resulting carbon radical appears to be transformed into a long-lived sulfur-centered radical via a 1,3-hydrogen shift. Analysis of the photoproducts indicates that the sulfur atom is the reactive center. Irradiation of 2', 3', 5'-tri-O-acetyl-5-iodo-4-thiouridine at 334 nm leads to the formation of disulfides and compounds resulting from the loss of iodide. See Wenska, G., et al., *J. Org. Chem.*, 70, 982-988 (2005).

The presently disclosed subject matter relates to the unexpected discovery that, upon further study, it has been found that 5-halo-4-thiouracil moieties are capable of forming fluorophores upon photoexcitation and subsequent crosslinking to other chemical moieties, such as, for example, pyrimidine groups.

II.C. Crosslinked Fluorophore

Disclosed herein is a novel fluorophore having the structure of Formula (I):

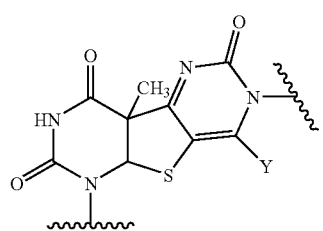

(I)

wherein:

Y is selected from the group consisting of H, $C_1$-$C_5$ linear or branched alkyl, cyano, nitro, carboxy, —$NR_1R_2$, —C(O)$R_3$, and —NH—C(O)—$R_4$, wherein $R_1$, $R_2$, $R_3$, and $R_4$ are selected from H and $C_1$-$C_5$ alkyl.

In some embodiments, the fluorphore is a moiety covalently linking a modified nucleoside or an oligonucleotide containing a modified nucleobase with another nucleoside or nucleic acid. Thus, in some embodiments, the fluorophore has a structure of Formula (Ia):

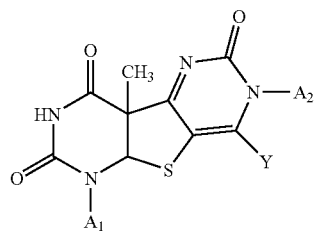

(Ia)

wherein:

Y is selected from the group consisting of H, $C_1$-$C_5$ linear or branched alkyl, cyano, nitro, carboxy, —$NR_1R_2$, —C(O)$R_3$, and —NH—C(O)—$R_4$, wherein $R_1$, $R_2$, $R_3$, and $R_4$ are selected from H and $C_1$-$C_5$ alkyl;

$A_1$ is selected from a sugar, a protected sugar, a partially protected sugar, and a nucleic acid; and $A_2$ is selected from a sugar, a protected sugar, a partially protected sugar, and an oligonucleotide.

In some embodiments, $A_1$ is a nucleic acid and $A_2$ is an oligonucleotide. In some embodiments, the sequences of $A_1$ and $A_2$ are at least 70% complementary. In some embodiments, the sequences of $A_1$ and $A_2$ are at least 80%, at least 90% or at least 95% complementary. In some embodiments, $A_1$ and $A_2$ are essentially complementary. Thus, in some embodiments, $A_1$ and $A_2$ are hybridized in an oligonucleotide duplex comprising one or more fluorescent covalent crosslinks.

In some embodiments, $A_1$ is a DNA. In some embodiments, $A_1$ is a gene, a subsequence of a gene, or a cDNA.

In some embodiments, the fluorophore is produced from two precursor molecules, wherein the first precursor molecule is a nucleic acid, and the second precursor molecule comprises an oligonucleotide sequence further comprising one or more 5-halo-4-thiouracil nucleobases. In general, these precursor molecules are not fluorescent, and, therefore, do not interfere with the fluorescence detection of the fluorophore. In some embodiments, the second precursor molecule comprises an oligonucleotide sequence having one or more 5-halo-4-thiouracil nucleobase located adjacent to one or more adenines (i.e., the probe comprises at least one residue comprising a 5-halo-4-thiouracil base, and that residue is directly adjacent to at least one adenine residue in the probe sequence). The adenine residue can be located in either the 3' or the 5' direction relative to the 5-halo-4-thiouracil nucleobase. In some embodiments, one of the one or more 5-halo-4-thiouracil nucleobases is adjacent to two adenine residues, one adjacent in the 3' direction and one adjacent in the 5' direction.

III. Crosslinked Fluorophore Uses

The presently disclosed subject matter provides methods for the detection of target molecules, such as target nucleic acids, through the formation and detection of a fluorescent covalent crosslink, wherein the fluorescent covalent crosslink comprises a fluorophore having a structure of Formula (I):

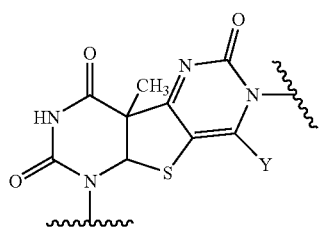

(I)

wherein:

Y is selected from the group consisting of H, $C_1$-$C_5$ linear or branched alkyl, cyano, nitro, carboxy, —$NR_1R_2$, —C(O)$R_3$, and —NH—C(O)—$R_4$, wherein $R_1$, $R_2$, $R_3$, and $R_4$ are selected from H and $C_1$-$C_5$ alkyl.

In some embodiments, the fluorescent covalent crosslink is formed following the photoexcitation (i.e., the irradiation) of a probe molecule.

In some embodiments, the probe molecule comprises an oligonucleotide sequence comprising one or more 5-halo-4-thiouracil nucleobases. Thus, in some embodiments, the method includes irradiating the probe molecule to excite a 5-halo-4-thiouracil moiety therein. Subsequently, the photoexcited 5-halo-4-thiouracil reacts with a moiety in the target molecule, forming the fluorescent covalent crosslink of Formula (I).

In some embodiments, the method comprises:

(a) contacting the probe molecule with the sample comprising the target nucleic acid, wherein the probe molecule hybridizes to the target nucleic acid in the sample to form an oligonucleotide duplex;

(b) irradiating the oligonucleotide duplex for a period of time to form one or more covalent bonds between the probe molecule and the target nucleic acid to form the fluorescent crosslinked product; and (c) detecting fluorescence of the fluorescent crosslinked product at a chosen emission wavelength, thereby determining the presence of a target nucleic acid molecule in the sample.

The 5-halo-4-thiouracil nucleobase can be incorporated into the oligonucleotide sequence of the probe molecule as a replacement for any nucleobase. Thus, in some embodiments, each of the one or more 5-halo-4-thiouracil nucleobases comprises a structure of formula (II):

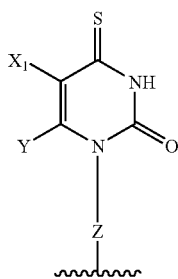

(II)

wherein:

$X_1$ is halo;

Y is selected from the group consisting of H, $C_1$-$C_5$ linear or branched alkyl, cyano, nitro, carboxy, —$NR_1R_2$, —C(O)$R_3$, and —NH—C(O)—$R_4$, wherein $R_1$, $R_2$, $R_3$, and $R_4$ are selected from H and $C_1$-$C_5$ alkyl; and Z is selected from the group consisting of ribose, 2'-deoxyribose, 2'-O-methyl ribose and morpholino.

In some embodiments, $X_1$ is fluoro, chloro, or bromo.

In some embodiments, Y is H and $X_1$ is fluoro or chloro.

In some embodiments, Z is ribose and has the structure:

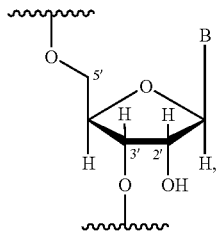

wherein B is a 5-halo-4-thiouracil. The structure of Formula (II) can thus be incorporated into the oligonucleotide sequence of the probe molecule by phosphate linkages at the 5' and 3' ribose oxygens. When Z is 2'-O-methyl ribose, the hydroxyl group at the 2' carbon is replaced by a methoxy (—$OCH_3$) group.

In some embodiments, Z is 2'-deoxyribose and has the structure:

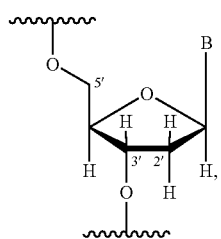

wherein B is a 5-halo-4-thiouracil. As when Z is a ribose, the deoxyribose is linked to the oligonucleotide backbone through covalent phosphate linkages at the oxygens of the 5' and 3' carbons When Z is morpholino, Z has the structure:

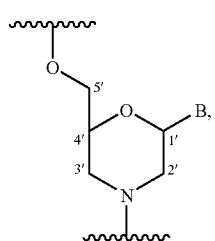

wherein B is a 5-halo-4-thiouracil. Additional information about the use of moropholino groups in place of pentose sugars in oligonucleotides is further described in U.S. Pat. No. 5,142,047 to Summerton et al., herein incorporated by reference.

In addition to ribose, 2'-deoxyribose, 2'-O-methyl ribose, and morpholino, the Z group or the pentose sugar of one or more of the other nucleotides in the probe sequence can also be any other group known to one of skill in the art as a replacement for ribose or deoxyribose in nucleotides. For example, the ribose 2' hydroxyl can be substituted by other chemical moieties, including, but not limited to alkyl, alkenyl, alkaryl, —O-alkaryl, —O-aralkyl, —$SCH_3$, cyano, —$CF_3$, heterocycloalkyl, aminoalkyl, substituted silyl, an RNA cleaving group, an intercalator, or a group for improving the cellular delivery of the probe. The 2' modification can be in the arabino (up) position or the ribo (down) position. Additional groups that can be substituted at the 2' position of Z or of the sugar in one or more of the other nucleotide residues in the probe include alkoxyalkoxy groups, such as 2'-methoxyethoxy (i.e., 2'—O—$CH_2CH_2OCH_3$, also known as 2'-MOE); 2'-dimethylaminooxyethoxy (i.e., 2'-O($CH_2$)$_2$ON($CH_3$)$_2$, also known as a 2'-DMAEOE group) and 2'-aminopropoxy (i.e., 2'-O$CH_2CH_2CH_2NH_2$). Another additional sugar modification is a locked nucleic acid (LNA) in which the 2' hydroxy group is linked to the 3' or 4' carbon atom of the sugar ring by a (—$CH_2$)$_n$— alkylene group wherein n is 1 or 2. The probes can also include peptide nucleic acid (PNA) sequences.

Further modifications can be made to the ribose phosphate backbone of the probe to increase the nuclease stability of the resulting probe. Examples of such modifications include the incorporation of methyl phosphonate, phosphorothioate, or phosphoroditioate linkages between one or more of the nucleotide residues of the probe sequence. Still more examples of modifications of the ribose phosphate backbone include the incorporation of siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate and/or sulfone internucleotide linkages, or 3'-3', 5'-2', or 5'-5' linkages.

In the methods of the presently disclosed subject matter, the precursors (i.e., the target nucleic acid and the probe molecule) of the fluorescent covalent crosslinked product are generally non-fluorescent. In particular, the probe molecules of the presently disclosed subject matter do not emit light at a wavelength that interferes with the fluorescence detection of the fluorescent covalent crosslink comprising a fluorophore having a structure of Formula (I). Thus, the presently disclosed methods can be used without having to subtract or otherwise eliminate background fluorescence.

In some embodiments, Z is ribose and the probe molecule comprises one or more nucleotide comprising 5-halo-4-thiouracil, independently selected from 5-fluoro-4-thiouridine or 5-chloro-4-thiouridine.

In some embodiments, the one or more 5-halo-4-thiouracil nucleobase of Formula (II) is positioned in the oligonucleotide sequence of the probe molecule adjacent to a nucleotide residue comprising an adenine residue. This adenine residue can be adjacent in either the 5' or the 3' direction on the probe sequence. In some embodiments, both nucleotide residues flanking the residue comprising the 5-halo-4-thiouracil nucleobase comprise an adenine.

In some embodiments, the one or more 5-halo-4-thiouracil nucleobase is adjacent to nucleotide residues other than adenine. The one or more 5-halo-4-thiouracil can be adjacent to one or more non-natural nucleotide residues or to natural nucleotide residues other than adenine. For example, the one or more 5-halo-4-thiouracil can be adjacent to a guanine residue that forms a guanine-thymidine mismatch with a thymidine residue in the target nucleic acid.

In some embodiments, the oligonucleotide sequence of the probe molecule is at least 70% complementary to the target nucleic acid. In some embodiments, the probe oligonucleotide sequence is at least 80%, at least 90% or at least 95% complementary to the target nucleic acid. In some embodiments, the probe molecule is essentially complementary to the target nucleic acid sequence. In some embodiments, the probe oligonucleotide sequence has a sequence such that, using a particular set of hybridization conditions, the probe will only hybridize to a single (i.e., a unique sequence) nucleic acid in a sample.

A variety of hybridization conditions can be used, including high, moderate and low stringency conditions; see for example Maniatis et al., Molecular Cloning: A Laboratory Manual, 2d Edition, 1989, and Short Protocols in Molecular Biology, ed. Ausubel, et al., $5^{th}$ Edition, Wiley, 2002, which are hereby incorporated by reference in their entirety. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993), which is incorporated herein by reference in the entirety. Generally, stringent conditions are selected to be about 5-10° C. lower than the thermal melting point ($T_m$) for the specific sequence at a defined ionic strength and pH. Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also can be achieved with the addition of helix destabilizing agents, such as formamide. The hybridization conditions also can vary when a non-ionic backbone, e.g., PNA, is used, as is known in the art.

In general, the oligonucleotide sequence of the probe molecule is 10 or more nucleotides in length. In some embodiments, the oligonucleotide sequence is 10 to 50 nucleotides in length. In some embodiments, the oligonucleotide sequence is 20 to 50 nucleotides in length. In some embodiments, the oligonucleotide sequence is 50 to 100 nucleotides in length.

In some embodiments, the oligonucleotide sequence of the probe molecule is greater than 100 nucleotides in length. Thus, in some embodiments, the probe sequence is up to 200, up to 300, up to 400, or up to 500 nucleotides in length.

In some embodiments, the contacting step takes place in a cell. Thus, in some embodiments, the probe is introduced into a living or fixed cell in which the target nucleic acid is present or is suspected of being present. Upon irradiation of the cell for a period of time, detection of fluorescence in the cell indicates the presence of the target nucleic acid. Accordingly, the presently described methods and probes provide a technique that can be used in fluorescence in situ hybridization (FISH) methods, providing the added benefit that the detection of fluorescence will only occur following sequence specific hybridization with a target molecule, and does not rely on an additional fluorescent reporter molecule, such as a fluorescently tagged antibody that binds to a group on the probe. Thus, the presently disclosed probes can be introduced into metaphase or interphase cells to detect gene or chromosomal abnormalities associated with various genetic diseases or with an increased risk for certain cancers. The presently disclosed methods can also be used to study DNA repair enzymes, for example, in the study of cellular responses to radiation and carcinogens, as well as the in the treatment of diseases such as cancer, as many cancer drugs yield interstrand crosslinks. Therefore, in some embodiments, the presently disclosed methods can be used in the study of excision repair, either in vitro or in vivo. For a recent review related to DNA interstrand crosslink formation and repair, see Noll, D. M., et al., Chem. Reviews, 106, 277-301 (2006).

In some embodiments, both the probe molecule and the target nucleic acid are in solution. In some embodiments, either the target nucleic acid or the probe is immobilized on a solid support. Solid supports useful for the immobilization of probes or target molecules include flat surfaces, including glass slides or silicon chips, beads, resins, gels, microspheres, nanoparticles, wells, microtiter plates, and fibers. Methods and nucleic acid chemical modifications for attaching the probes or target molecules to the solid support will be understood by one of skill in the art and are discussed in further detail hereinbelow.

In some embodiments, the presently disclosed methods further comprise determining an amount of the target nucleic acid in the sample. For example, the fluorescence intensity of the fluorescent crosslinked product produced using a given set of irradiation and hybridization conditions can be compared to the fluorescence intensity of the fluorescent crosslinked product produced from the hybridization and irradiation of the probe molecule with a known concentration of target nucleic acid under using the same conditions. Alternatively, the fluorescence intensity of the fluorescent crosslinked product can be compared with the fluorescence intensity of a standard curve of varying concentrations of fluorescent crosslinked product.

In some embodiments, the method includes a step for separating the oligonucleotide duplex containing the fluorescent covalent crosslinked product from non-duplexed nucleic acids and non-duplexed probe molecules after the irradiating step. Additional sequence or other structural or biological data can be obtained from the isolated oligonucleotide duplexes. For example, determining the amount of the fluorescent crosslinked product can take place following the separation of the oligonucleotide duplexes. The separated duplexes can be subjected to gel electrophoresis, enzymatic digestion, mass spectroscopy, antibody-based assays, and other methods known in the art to study nucleic acid structure.

Because the probe molecules of the presently disclosed methods do not comprise a fluorescent label and the fluorescently crosslinked product is only formed following irradiation of the probe molecule, the currently disclosed methods can involve zero background fluorescence. Accordingly, the presently disclosed methods can be employed without the use of washing steps to remove excess probe molecule following hybridization.

In some embodiments, the irradiation step is performed at a wavelength longer than about 280 nanometers. Thus, in some embodiments, the one or more 5-fluoro-4-thiouracil nucleobase in the probe is selectively photoactivated. In some embodiments, the irradiating step is performed with a UV light source. The amount of time a duplex is irradiated and the flux with which a duplex is irradiated can be adjusted to provide complete photocrosslinking of the two strands of the duplex. These parameters will depend, in part, upon the sequences of the strands in the duplex.

In some embodiments, the irradiating step can be performed over a range of wavelengths. In some embodiments, the irradiating step is done at a single specific wavelength. The single specific wavelength can be chosen to correspond with the maximum absorption of a specific 5-halo-4-thiouracil nucleobase. For example, in some embodiments, $X_1$ is Cl and Y is H, and the irradiating step is performed at a wavelength of 366 nm.

In some embodiments, the presently disclosed methods further comprise amplifying one or more nucleic acid in the sample prior to contacting the probe molecule with the sample. Amplification of the sample can be done using one or more rounds of PCR amplification, using either random or specific primers. All of the nucleic acids present within a sample can be amplified. Alternatively, one or more target nucleic acids can be amplified preferentially or exclusively.

Target nucleic acids that can be detected according to the presently disclosed methods include animal, bacterial, fungal, human, parasitic, plant and viral nucleic acids. The target nucleic acid can be DNA or RNA. In some embodiments, the target nucleic acid is DNA selected from the group consisting of genomic DNA and cDNA. Thus, in some embodiments, determining the presence of a target nucleic acid determines the presence of a gene or of foreign DNA in a cell.

In some embodiments, the target nucleic acid is an RNA selected from the group consisting of tRNA, rRNA, mRNA, siRNA, micro-RNA and a non-coding RNA. In some embodiments, determining the presence of a target nucleic acid determines the up-regulation or down-regulation of a given gene.

In some embodiments, the target nucleic acid is a subsequence of a longer RNA or DNA. For example, the target nucleic acid can comprise a unique subsequence of a gene or cDNA.

The samples of the presently disclosed subject matter include both biological samples and environmental samples. For example, suitable biological samples include cells (both living and fixed), cell extracts, tissues, tissue extracts, and various biological fluids, including blood, plasma, cerebrospinal fluid (CSF), saliva, semen, milk, feces, and urine. Suitable samples can be taken by means of biopsies, swabs, hair or skin samples. A sample can be a single cell. Samples can be taken from fetal or embryonic tissue, from bone marrow or from germ cells or a tissue in an adult or developing organism.

In some embodiments, the biological sample can be obtained from a subject. The term "subject" can include all vertebrate animals. In some embodiments, the subject can be avian or mammalian. Suitable subjects include animals having social importance (e.g., as pets or in zoos) or that have economic importance (e.g., animals raised on farms for human consumption), as well as endangered animals (such as Siberian tigers). Thus, avian subjects include parrots, fowl, particularly to domesticated fowl, i.e., poultry, such as turkeys, chickens, ducks, geese, guinea fowl, and the like. Avian subjects can also include wild birds, especially wild birds suspected of or having a risk of harboring a pathogen, such as a viral, protozoal, or bacterial pathogen. Suitable mammalian subjects include carnivores (such as cats and dogs), ruminants (such as cattle, oxen, sheep, giraffes, deer, goats, bison, and camels), swine (pigs, hogs, and wild boars), and horses (including racehorses). Thus, in some embodiments, the present methods can be used for diagnostic testing or biological research related to livestock, including, but not limited to, domesticated swine (pigs and hogs), ruminants, horses, poultry, and the like.

In some embodiments the biological sample is from a human subject.

Environmental samples include samples such as tap water, wastewater, well water, river water, lake water, soil, air and material collected from household surfaces. Material collected from household surfaces includes material collected (for example swabbed) from metal, plastic, wood, ceramic, or fabric surfaces found in the home. In particular, such surfaces can include those at high risk for harboring bacterial and viral pathogens, such as surfaces in bathrooms and kitchens (e.g., cutting boards, counter tops, utensils, lighting or plumbing fixtures, dishtowels, kitchen sponges, and the like). Similarly, samples can also be collected from surfaces in offices, schools, laboratories, public places, and industrial sites.

Thus, in some embodiments, the presently disclosed methods can be used to determine the presence of a target nucleic acid that is indicative of the presence of a disease, the absence of a disease, the potential future presence of a disease, the progression of a disease, the regression of a disease, and combinations thereof. In some embodiments, determining the presence of a target nucleic acid is indicative of the presence of one of the group consisting of a virus, a bacteria, a fungus, a parasite, and combinations thereof. In some embodiments, the presently disclosed methods can be used in gene expression studies. Thus, the methods can be used to follow differential expression of genes as the result of the progression of a disease, the regression of a disease, the action of a pharmaceutical agent or other medical treatment, aging, and the like.

IV. Synthesis of Probes for Forming Crosslinked Fluorophores

5-Halo-4-thiouridines can be synthesized, for example, from their oxo-analogues via $P_2S_5$ thionation. See Wenska, G., J., et al., Chem. Soc., Perkin Trans 1, 53-57 (2002). An alternative route to the 5-halo-4-thiouridines involves a β-cyanoethyl (—$CH_2CH_2CN$) protected intermediate, which can be prepared by first reacting the uridine with an arylsulfonyl chloride, followed by displacement of the sulfonyl group with 3-mercaptopropionitrile. See Coleman, R. S., and Kesicki, E. A., *J. Am. Chem. Soc.*, 116, 11636-11642 (1994). Additional routes to the 5-halo-4-thiouridines and to protected 5-fluoro-4-thiouridines suitable as synthons for the preparation of oligonucleotide probes will be understood to one of skill in the art of synthetic organic chemistry and nucleic acid synthesis upon a review of the present disclosure.

5-Halo-4-thiouridine nucleotides can be incorporated into oligonucleotide probes using either chemical synthesis (either solid-phase or solution-phase) or using enzymatic synthesis, including template directed synthesis. Probes containing 5-fluoro-4-thiouridines can be synthesized de novo, or the modified nucleotides can be incorporated into naturally occurring sequences, including partially digested sequences of naturally occurring oligonucelotides.

In some embodiments, the 5-halo-4-thiouridines can be incorporated into oligonucleotide sequences according to techniques known in the art for the solid-phase synthesis of oligonucleotides. For a review of such chemistry, see "Oligonucleotide Synthesis, A Practical Approach," M. J. Gait, ed., IRL Press Ltd, Oxford, Great Britain, 1984, which is herein incorporated by reference. For example, a 5-halo-4-thiouracil can be incorporated into both DNA and RNA by substitution of a 5-halo-4-thiodeoxyuracil and a 5-halo-4-thiouracil for thymine and uracil, respectively, using the phosphoramidite or the H-phosphonate method. Additional methods related to solid phase oligonucleotide synthesis are described in, for example: Beaucage, S. L., and Iyer, R. P., *Tetrahedron*, 48, 2223-2311 (1992); U.S. Pat. No. 5,026,838 to Nojiri, R., et al.; and U.S. Pat. No. 4,973,679 to Caruthers, M. H., and Beaucage, S. L.

In some embodiments, a sulfur-protected nucleotide synthon can be used. In some embodiments, the sulfur of the thiocarbonyl group of is protected by a β-cyanoethyl group or by another group that can be removed by a β-elimination mechanism. Other suitable sulfur protecting groups for thiocarbonyl groups include the S-(pivaloyloxy)methyl group and the S-dinitrophenyl group. See, Favre, A., et al., *J. Photochem. Photobiol. B*, 42, 109-124 (1998); and Coleman, R. S., and Kesicki, E. A., *J. Am. Chem. Soc.*, 116, 11636-11642 (1994). Further, based on studies of the chemical incorporation of 4-thiouracil into oligonucleotides, it appears that no sulfur protecting group is required if t-butyl hydroperoxide is used in place of the usual iodine/water reagent in the oxidation step of phosphoramidite-based syntheses. See Kumar, R. K., and Davis, D. R., *Nucleic Acids Res.*, 25, 1272-1280 (1997). Thus in some embodiments, a nucleotide synthon without a sulfur protecting group can be used.

The 5-halo-4-thiouracil nucleotide synthon can be incorporated into oligonucleotides using an appropriate polymerase system. For example, RNA containing a 5-halo-4-thiouridine can be prepared using a 5-halo-4-thiouridine triphosphate with T7 RNA polymerase and a DNA template. A 5-halo-4-thiouridine-containing oligonucleotide sequence can also be ligated onto another sequence using T4 DNA polymerase and a bridging deoxyoligonucleotide sequence. See, Favre. A., et al., *J. Photochem. Photobiol. B*, 42, 109-124 (1998).

Accordingly, provided herein are methods of synthesizing probe molecules that form a fluorescent covalent crosslinked product of Formula (I) with a target molecule, such as, but not limited to, target nucleic acids or nucleosides. In some embodiments, the method of synthesizing probe molecules that form a fluorescent covalent crosslinked product comprising a structure of Formula (I):

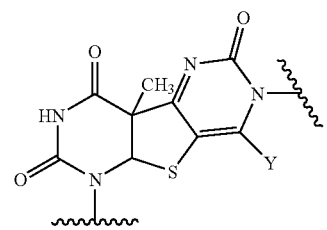

(I)

wherein:

Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and $R_4$ are selected from H and $C_1$-$C_5$ alkyl;

comprises incorporating into an oligonucleotide sequence one or more nucleotide synthons having a structure of Formula (III):

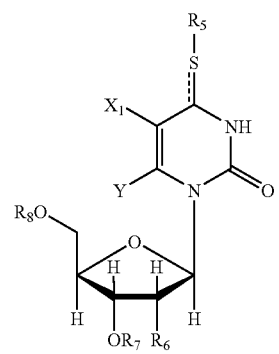

(III)

wherein:

$X_1$ is halo;

Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and $R_4$ are selected from H and $C_1$-$C_5$ alkyl;

$R_5$ is present or absent, and when present is a suitable sulfur protecting group;

$R_6$ is selected from the group consisting of H, hydroxy, and —$OR_{10}$, wherein $R_{10}$ is a suitable hydroxyl protecting group or alkyl;

$R_7$ is selected from the group consisting of

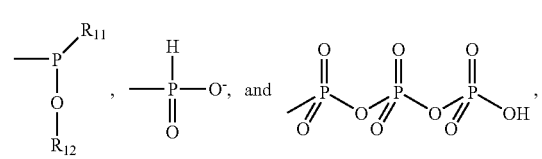

wherein $R_{11}$ is a secondary amino group; and $R_{12}$ is selected from the group consisting of allyl and —$CH_2CH_2R_{13}$, wherein $R_{13}$ is selected from the group consisting of cyano, nitro, halo, thiocyano, alkylsulfonate, and arylsulfonate; and $R_8$ is H or a suitable hydroxyl protecting group.

Suitable hydroxyl protecting groups are groups that can replace the hydrogen atom of the hydroxyl (—OH) group. Suitable hydroxyl protecting groups are any that can protect the hydroxyl group during synthesis of the oligonucleotide probe and may be removed under conditions that do not affect the final probe. In some embodiments, a given hydroxyl protecting group can be removed under conditions that do not affect (i.e. remove) any of the other protecting groups on the synthon or any portion of the probe molecule being synthesized. In some embodiments, suitable hydroxyl protecting group can be selected from the group consisting of trityl, monomethoxytrityl, dimethoxytrityl, trimethylsilyl, triethylsilyl, triphenylsilyl, t-butyldimethylsilyl, tetrahydropyranyl, 4-methoxyhydrofuranyl, benzoyl, benzyl, tetrahydrofuranyl, methoxymethyl, methoxyethoxymethyl, phenoxymethyl, methylthiomethyl, and phenylthiomethyl.

In some embodiments, $R_{10}$ is methyl.

In some embodiments, $R_5$ is present. In some embodiments, the suitable sulfur protecting group is —$CH_2CH_2R_9$, wherein $R_9$ is selected from the group consisting of cyano, nitro, halo, thiocyano, alkylsulfonate, and arylsulfonate. In some embodiments, the suitable sulfur protecting group is selected from 2,4-dinitrophenyl (i.e., —$C_6H_3(NO_2)_2$) and pivaloyloxymethyl (i.e., —$CH_2OC(O)(CH_3)_3$). In some embodiments, $R_5$ is β-cyanoethyl (i.e., —$CH_2CH_2CN$). In some embodiments, $R_5$ is not present and the sulfur atom is attached to the ring via a carbon-sulfur double bond.

In some embodiments, $X_1$ is bromo, chloro, or fluoro.

In some embodiments, the method comprises chemical synthesis using phosphoramidite chemistry. In some embodiments, $R_7$ is

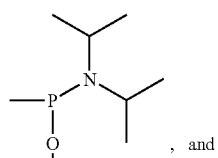, and $R_8$ is

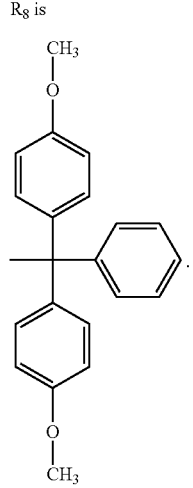

In some embodiments, the synthesizing is enzymatically catalyzed and $R_7$ is

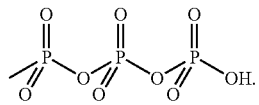

Sulfur and hydroxyl protecting groups can be removed during the course of oligonucleotide synthesis or following completion of the synthesis. For example, when $R_8$ is a suitable hydroxyl protecting group, it is generally removed during the course of oligonucleotide synthesis, following addition of the synthon to a growing oligonucleotide sequence.

Accordingly, the presently disclosed subject matter describes methods of synthesizing probes for use in oligonucleotide sequencing, as well as in identifying contacts within nucleic acids, such as in probing the structure of RNA in solution, and for identifying contacts between nucleic acids and proteins in nucleoprotein assemblies. Thus, the probes can be used as biological research tools and in medical diagnostics, for example, in detecting single nucleotide polymorphisms or in gene expression studies.

V. Arrays

In some embodiments, the presently disclosed subject matter provides an array for determining the presence of one or more target nucleic acid by detecting the presence of a fluorescent crosslinked product, said fluorescent crosslinked product comprising a structure of Formula (I):

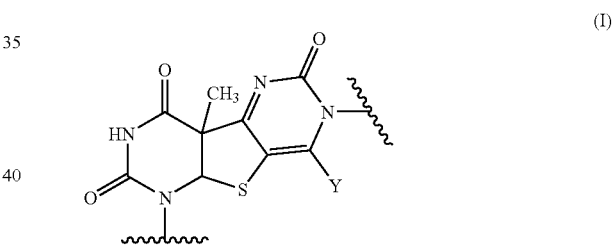

(I)

wherein:
Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and $R_4$ are selected from H and $C_1$-$C_5$ alkyl;

wherein the array comprises:
(a) a solid support; and
(b) a probe set comprising two or more probe molecules, each probe molecule comprising an oligonucleotide sequence comprising one or more 5-halo-4-thiouracil nucleobases, wherein:
  (i) each of the two or more probe molecules comprises an oligonucleotide sequence at least 70% complementary to a different target nucleic acid sequence; and
  (ii) the two or more probe molecules are immobilized on the solid support.

In some embodiments, each of the two or more probe molecules is immobilized at a different discrete, known location on the solid support. Thus, detection of a fluorescent signal at a particular array address will be indicative of the hybridization of a target nucleic acid having a sequence complementary to the probe sequence at that address.

In some embodiments, the probe set can comprise up to five, up to ten, up to 50, up to 100, up to 1000, or more than 1000 unique probe molecules, each having a complementary sequence to a different known or suspected target nucleic acid sequence.

Generally, the array support can be any support that contains a plurality of addresses suitable for the synthesis or deposition of nucleic acid or nucleic acid analog oligomer probes. The support can be rigid or flexible and will comprise a substrate suitable for depositing or synthesizing oligonucleotide probes. The substrate can be glass, plastic, polymer, biological, non-biological, organic, or inorganic materials suitable for depositing or synthesizing oligonucleotides. Arrays can take the forms of multiwell plates, microtiter plates, microarray plates, particles, strands, gels, tubing, spheres, containers, capillaries, pads, slices, films, or slides. The substrate and its surface can also be chosen to provide appropriate light-absorbing characteristics. For instance, the substrate may be a polymerized Langmuir Blodgett film, functionalized glass, Si, Ge, GaAs, GaP, $SiO_2$, modified silicon, or any one of a wide variety of gels or polymers such as (poly)tetrafluoroethylene, (poly)vinylidenedifluoride, polystyrene, polycarbonate, or combinations thereof. Other suitable substrate materials will be readily apparent to those of skill in the art upon review of this disclosure.

Arrays can be made by covalently binding the oligonucleotide probes to the substrate, for example by covalently attaching the oligomers to a chemical group (e.g., an amine or hydroxyl) on the substrate. The substrate can be an activated substrate, such as, but not limited to, a cyanogen bromide (CNBr) activated matrix or substrate, The probe can also be chemically modified at the 3' or 5' end to enhance covalent binding with the substrate or activated substrate. Suitable 3' or 5' modifications include amino and thiol groups. Additionally, one or both of the probe and the substrate can comprise a functionalized tether moiety, including reactive end groups for attachment to the support and to the probe and a variable spacer portion, such that the attached probe is not directly attached to the substrate. Spacer portions can include alkylene and polymer groups, such as, but not limited to, polyethylene glycol. Arrays can also be synthesized by the non-covalent attachment of probes to the support, for example through electrostatic interactions.

When arrays of pre-synthesized probes are formed, the pre-synthesized probes can be place on the array one probe at a time, for example, using a micropipette, or by using an array of pipettes or capillary pins or some other dispenser, so that several probes are placed on the array simultaneously. Robotic systems can be used to place the probes on the substrate with a high degree of accuracy. Alternatively, the pre-synthesized probes can be deposited at specific sites on the array using masking techniques (i.e., covering the portions of the array where the presence of the probe is not desired). In another embodiment the method for making arrays includes synthesizing the oligomers directly on the substrate.

EXAMPLES

The following Examples have been included to provide illustrations of the presently disclosed subject matter. In light of the present disclosure and the general level of skill in the art, those of skill will appreciate that the following Examples are intended to be exemplary only and that numerous changes, modifications and alterations can be employed without departing from the spirit and scope of the presently disclosed subject matter.

Materials and Methods for Examples

Synthesis of Modified Nucleotides

The synthesis of 5-fluoro-4-thiouridine has been previously described. See Wenska, G., et al., *J. Chem. Soc., Perkin Trans.* 1, 53-57 (2002); and Taras-Goślińska, K., et al., *J. Photochem. Photobiol. A: Chem.* 168, 227-233 (2004). Briefly, 5-fluorouridine obtained from Aldrich (Aldrich Chemical Company, Milwaukee, Wis., United States of America) was acetylated according to previously published procedures. See Zemlicka, J., et al., *Collect. Czech Chem. Commun.*, 29, 635 (1964). 2',3',5'-Tri-O-acetyl-5-fluorouridine was purified by column chromatography using Merck silica gel 60 (70-230 mesh). HPLC preparation was performed on a Waters 600E instrument (Waters Corporation, Milford, Mass., United States of America). 2',3',5'-Tri-O-acetyl-5-fluorouridine (2 mM) was treated with $P_2S_5$ (6 millimolar) in peroxide free dioxane. Solvent was removed under reduced pressure and the residue was extracted with chloroform ($CH_3Cl$) and purified by flash chromatography followed by HPLC. The sugar-protected 5-fluoro-4-thiouridine was prepared by standard methods including a 5'-dimethoxytrityl and 3'-phosphoramidite.

Synthesis of Probe Molecules

Five oligonucleotide sequences were prepared for use in the Examples below. The sequences of the oligonucleotides are shown below in Table 1. The oligonucleotides were synthesized using standard phosphoramidite methods using a Applied Biosystems 391 PCR-MATE (Applied Biosystems, Foster City, Calif., United States of America). The synthesis followed standard methods, however, the final cleavage and deprotection step was carried out in anhydrous methanol ammonia solvent.

TABLE 1

Oligonuceotide Sequences

| SEQ ID No. | Sequence | Identity of modified nucleobase | Use |
|---|---|---|---|
| 1 | 5'd-TTATCGTATCGT | — | Model DNA target |
| 2 | 5'-CGA(FSU)A | 5-fluoro-4-thiouridine | pentamer probe |
| 3 | 5'-CGA(4tU)A | 4-thiouridine | pentamer control probe |
| 4 | 5'-CGA(FSU)ACGAUA | 5-fluoro-4-thiouridine | decamer probe |
| 5 | 5'-CGA(4tU)ACGAUA | 4-thiouridine | decamer control probe |
| 6 | 5'-CGATACGA(FSU)A | 5-fluoro-4-thiouridine | decamer probe |

HPLC Studies

HPLC chromatography was performed using a Waters 600E instrument equipped with a Waters 991 Photodiode Array UV detector using a Waters XTERRA® RP18 column 3.5 μm (4.6×150 mm) columns for analytical studies involving nucleic acids or a Waters NOVA-PAK™ C18 4 mm, (4.6×250 mm column) for analytical studies involving nucleotides (Waters Corporation, Milford, Mass., United States of America). For all oligonucleotide separations the conditions were as follows:

Buffer A: 0.1 M CH$_3$COONH$_4$+10 mM tetrabutylammonium hydrogen sulfate (TBAHS);

Buffer B: 0.1 M CH$_3$COONH$_4$+10 mM TBAHS, 50% CH$_3$CN.

Gradient elution, initial 65% A and 35% B; final 100% B (30 min); flow rate 0.8 mL/min.

NMR Studies $^1$H NMR, $^{13}$C NMR and NOE difference spectra were recorded on a Varian UNITY 300™ spectrometer (Varian, Inc., Palo Alto, Calif., United States of America). HMBC and HMQC spectra were recorded on a Bruker AVANCE™ 600 spectra (Bruker Biospin Corporation, Billerica, Mass., United States of America). All chemical shifts are in ppm relative to tetramethylsilane as an internal standard and coupling constants are in hertz (Hz).

Example 1

Scheme 2. Possible Hybridization Between the Target and Pentamer Probes.

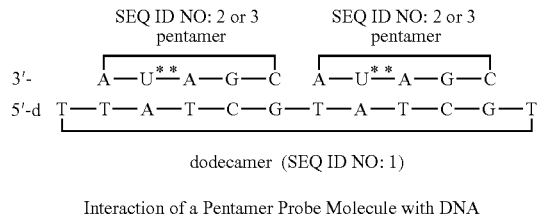

dodecamer (SEQ ID NO: 1)

Interaction of a Pentamer Probe Molecule with DNA

A solution containing a model target nucleic acid, 5'd-TTATCGTATC GT (SEQ ID NO: 1) and a model pentamer probe molecule, 5'-CGA(FSU)A (SEQ ID NO: 2) was prepared in phosphate buffer (pH=7.0). The ratio of probe to target was 2:1.2. An analogous solution comprising the target nucleic acid (SEQ ID NO: 1) and a pentamer control probe, 5'-CGA(4tU)A (SEQ ID NO: 3), was also prepared.

FIGS. 1A-1D show absorption spectra and melt curves for the hybrids formed from the hybridization of the target sequence (SEQ ID NO: 1) and either the pentamer probe containing the 5-fluoro-4-thiouridine (SEQ ID NO: 2) or the pentamer control probe containing 4-thiouridine (SEQ ID NO: 3). As indicated in Scheme 2, above, two molecules of either of the two pentamer probes (SEQ ID NO: 2 or SEQ ID NO: 3) can hybridize with one molecule of the target. U** in Scheme 2 indicates a modified nucleotide in the probe sequence (e.g., FSU or 4tU). The melt curves (FIGS. 1C and 1D) are approximately the same, indicating that the effects of 5-fluoro-4-thiouracil and 4-thiouracil on hybridization are equivalent.

Figure 1:
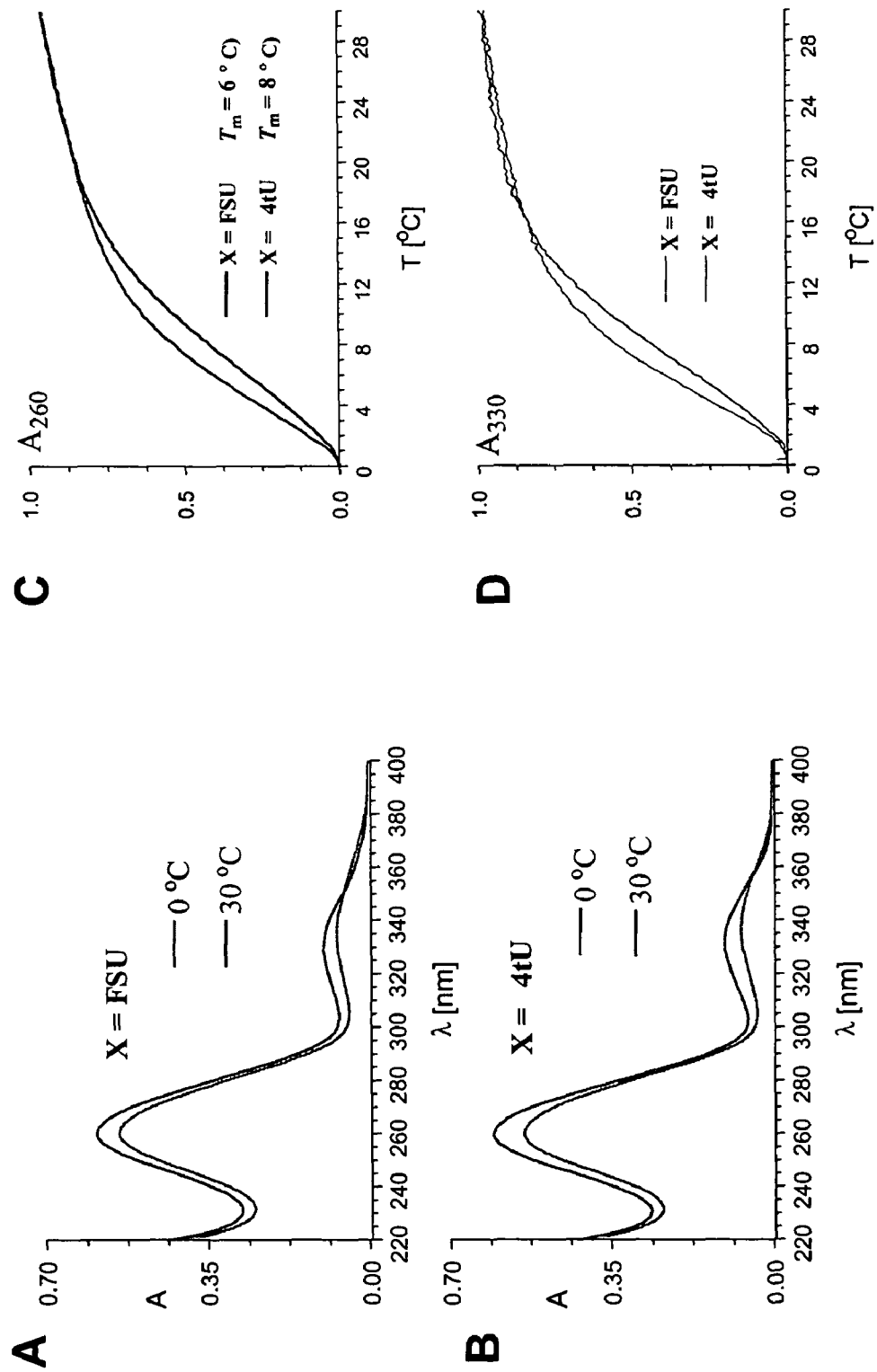
FIG. 1A shows ultraviolet (UV) absorption spectra of the duplex formed between the dodecamer target sequence, 5'd-TTATCGTATC GT (SEQ ID NO: 1), and the pentamer probe sequence, 5'-CGA(FSU)A wherein FSU is a 5-fluoro-4-thiouridine nucleotide residue (SEQ ID NO: 2). The upper line is the spectrum of the hybrid at 30° C., while the lower line is the spectrum of the hybrid at 0° C. X in the legend is the identity of the modified nucleotide (i.e., FSU).
FIG. 1B shows UV absorption spectra of the duplex formed between the dodecamer target sequence, 5'd-TTATCGTATC GT (SEQ ID NO: 1), and the pentamer control probe sequence, 5'-CGA(4tU)A wherein 4tU is a 4-thiouridine nucleotide residue (SEQ ID NO: 3). The upper line is the spectrum of the hybrid at 30° C., while the lower line is the spectrum of the hybrid at 0° C. X in the legend is the identity of the modified nucleotide (i.e., 4tU).
FIG. 1C is a graph showing the melting curves for the hybridized duplex of the dodecamer target sequence, 5'd-TTATCGTATC GT (SEQ ID NO: 1), and the pentamer probe sequence, 5'-CGA(FSU)A (SEQ ID NO: 2), and for the hybridized duplex of the dodecamer target sequence, 5'd-TTATCGTATC GT (SEQ ID NO: 1), with the pentamer control probe sequence, 5'-CGA(4tU)A (SEQ ID NO: 3), measuring absorbance at 260 nm. The duplex of the target (SEQ ID NO: 1) and the control probe with 4-thiouridine (SEQ ID NO: 3) melts at slightly higher temperature than the duplex of the target (SEQ ID NO: 1) and the 5-halo-4-thiouridine probe (SEQ ID NO: 2). X in the legend is the identity of the modified nucleotide (i.e., FSU or 4tU).
FIG. 1D is a graph showing the melting curves for the hybridized duplexes described in FIG. 1C, measuring absorbance at 330 nm. The duplex of the target (SEQ ID NO: 1) and the control probe (SEQ ID NO: 3) melts at slightly higher temperature than the duplex of the target (SEQ ID NO: 1) and the 5-halo-4-thiouridine probe (SEQ ID NO: 2). X in the legend is the identity of the modified nucleotide (i.e., FSU or 4tU).
Figure 2:
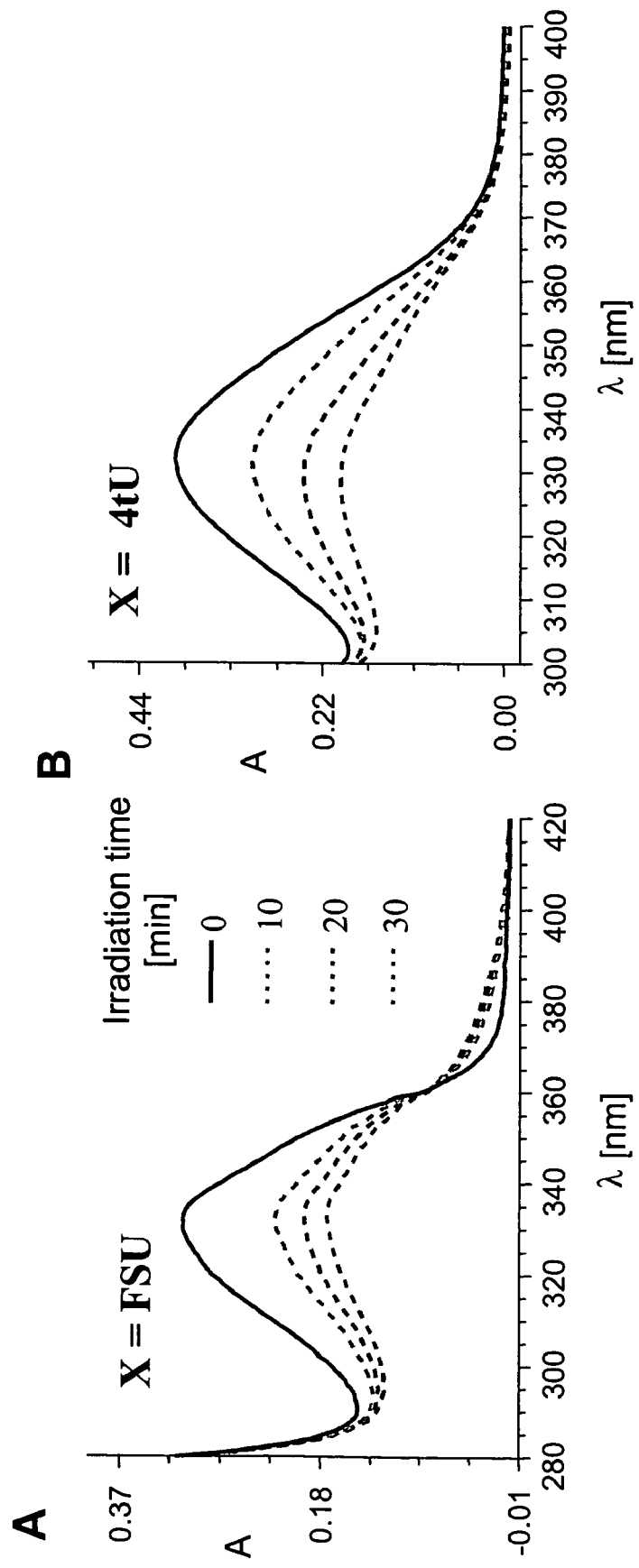
FIG. 2A shows absorption spectra of the hybridized duplex of the dodecamer target sequence, 5'd-TTATCGTATC GT (SEQ ID NO: 1), and the pentamer probe sequence, 5'-CGA(FSU)A (SEQ ID NO: 2), after irradiation at 366 nm for the indicated time periods. The solid line is the spectra after 0 min of irradiation. The lightest dashed line is the spectra after 10 min of irradiation. The darkest dashed line is the spectra after 20 min of irradiation. The medium dark dashed line is the spectra after 30 min of irradiation. X is the identity of the modified nucleotide (i.e., FSU).
FIG. 2B shows absorption spectra of the hybridized duplex or the dodecamer target sequence, 5'd-TTATCGTATC GT (SEQ ID NO: 1), and the pentamer control probe sequence, 5'-CGA(4tU)A (SEQ ID NO: 3), after irradiation at 366 nm for the indicated time periods. The solid line is the spectra after 0 min of irradiation. The lightest dashed line is the spectra after 10 min of irradiation. The darkest dashed line is the spectra after 20 min of irradiation. The medium dark dashed line is the spectra after 30 min of irradiation. X is the identity of the modified nucleotide (i.e., 4tU).

The hybrids were irradiated in a 4 mm×1 cm cuvette at 0° C. with a high pressure mercury lamp at 366 nm. FIG. 2A shows the absorption spectra of the hybrid solution comprising the target dodecamer (SEQ ID NO: 1) and the pentamer probe (SEQ ID NO: 2) after irradiation for different time periods. FIG. 2B shows the absorption spectra of the hybrid between the target dodecamer (SEQ ID NO: 1) and the pentamer control probe (SEQ ID NO: 3) following irradiation for different time periods. The spectra suggest that a crosslinked product is formed in both duplexes, as indicated by the decreasing absorption intensities attributable to the modified uracils.

Figure 3:
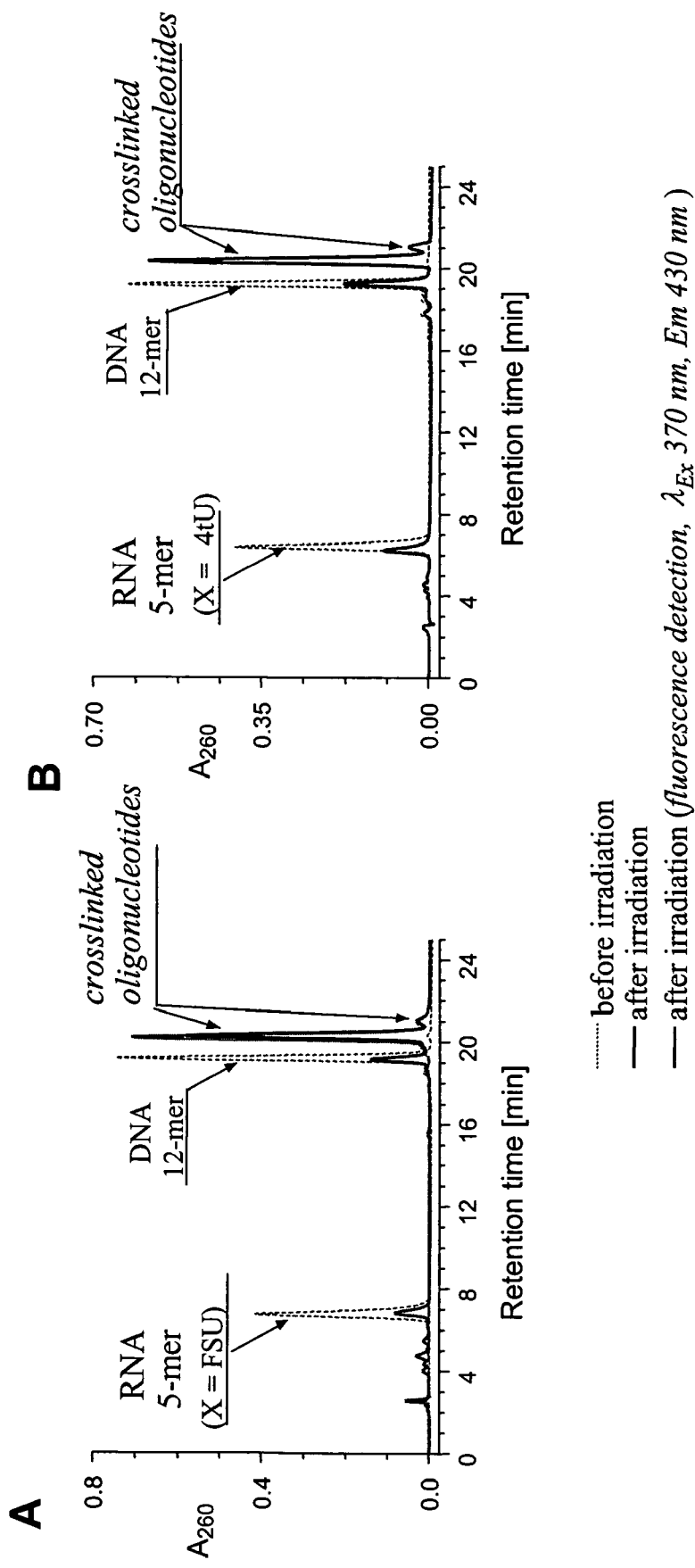
FIG. 3A is a composite HPLC chromatogram of the hybridization and irradiation of the dodecamer target sequence, 5'd-TTATCGTATC GT (SEQ ID NO: 1), and the pentamer probe sequence, 5'-CGA(FSU)A (SEQ ID NO: 2). The dotted line shows the chromatogram of the mixture before irradiation, measuring absorbance at 260 nm. The heavy line shows the chromatogram of the reaction mixture after irradiation, measuring absorbance at 260 nm. The lighter solid line shows the chromatogram of the mixture after irradiation, measuring fluorescence, using an excitation wavelength of 370 nm and observing fluorescence emission at 430 nm. X is the identity of the modified nucleotide (i.e., FSU).
FIG. 3B is a composite HPLC chromatogram of the hybridization and irradiation of the dodecamer target sequence, 5'd-TTATCGTATC GT (SEQ ID NO: 1), and the pentamer control probe sequence, 5'-CGA(4tU)A (SEQ ID NO: 3). The dotted line shows the chromatogram of the mixture before irradiation, measuring absorbance at 260 nm. The heavy line shows the chromatogram of the mixture after irradiation, measuring absorbance at 260 nm. X is the identity of the modified nucleotide (i.e., 4tU).

Formation of crosslinked product was also followed by HPLC chromatography. FIG. 3A shows the HPLC chromatogram of the photoreaction of the duplex of the target (SEQ ID NO: 1) and the pentamer probe (SEQ ID NO: 2). The photoreaction of the duplex of the target (SEQ ID NO: 1) and the pentamer control probe (SEQ ID NO: 3) is shown in FIG. 3B. HPLC conditions were: gradient elution, starting from 65% buffer A (50% 0.1 M CH$_3$COONH$_4$ with 10 mM TBAHS) and ending at 100% buffer B (50% 0.1 M CH$_3$COONH$_4$ with 10 mM TBAHS: 50% acetonitrile), at a flow rate of 0.8 mL/min. The column was a Waters XTERRA® RP18 3.5 µm (4.6×150 mm) (Waters Corporation, Milford, Mass., United States of America).

Figure 4:
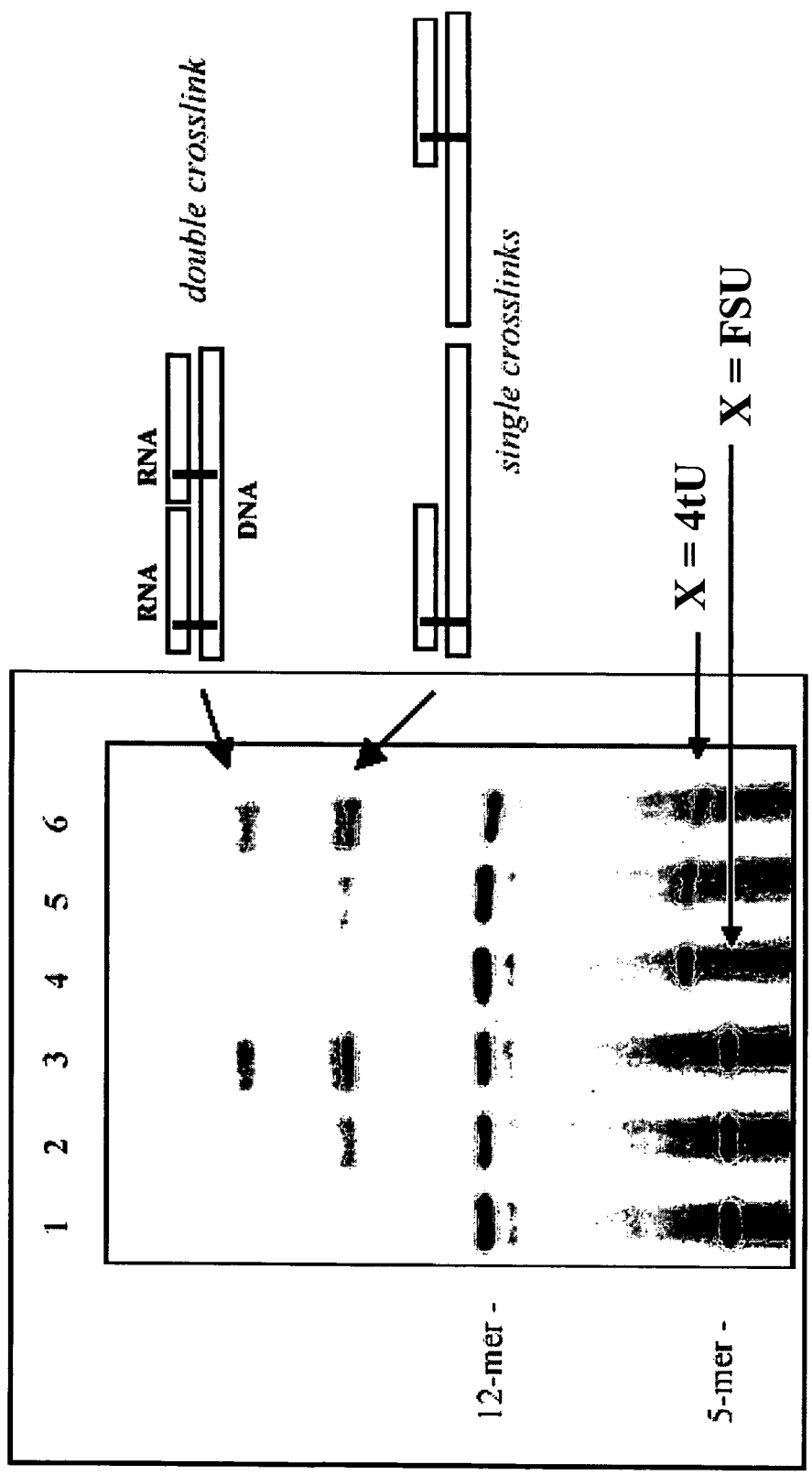
FIG. 4 is a digital image showing polyacrylamide gel electrophoresis (PAGE) analysis of the starting materials and photoproducts resulting from the hybridization and irradiation of each of the two pentamer probe sequences, 5'-CGA (FSU)A (SEQ ID NO: 2) or 5'-CGA(4tU)A (SEQ ID NO: 3) with the dodecamer target sequence, 5'd-TTATCGTATC GT (SEQ ID NO: 1). Lane 1 is the gel of a solution of dodecamer target sequence, 5'd-TTATCGTATC GT (SEQ ID NO: 1), and the pentamer probe sequence, 5'-CGA(FSU)A (SEQ ID NO: 2). Lane 2 is the gel of the same mixture as lane 1, only after 10 minutes of irradiation at 366 nm. Lane 3 is the gel of the same mixture as in lanes 1 and 2, only after 40 minutes of irradiation. Lane 4 is the gel for a solution of the dodecamer target sequence, 5'd-TTATCGTATC GT (SEQ ID NO: 1), and the pentamer control probe, 5'-CGA(4tU)A (SEQ ID NO: 3). Lanes 5 and 6 are the gels of the same solution as in lane 4, after 10 and 40 minutes of irradiation at 366 nm, respectively. Photoadducts having approximate masses corresponding to duplexes having a single crosslink (i.e., one covalently attached pentamer) and those having two crosslinks (i.e., two covalently linked pentamers) are indicated by the arrows and figures on the right-hand side of the photograph. X is the identity of the modified nucleotide (i.e., FSU or 4tU).

The crosslinked products were also analyzed by polyacrylamide gel electrophoresis (PAGE) analysis. See FIG. 4. Lanes 1-3 show the duplex of the target (SEQ ID NO: 1) with the 5-fluoro-4-thiouridine-containing pentamer probe (SEQ ID NO: 2) at irradiation times of 0 min, 10 min, and 40 min, respectively. Lanes 4-6 show the duplex of the target (SEQ ID NO: 1) with the 4-thiouridine-containing pentamer control probe (SEQ ID NO: 3) at irradiation times of 0 min, 10 min, and 40 min, respectively. The products attributable to duplexes containing a single crosslink (from one probe molecule) and those corresponding to duplexes with two crosslinks (one from each of two probe molecules attached to the same target molecule) are indicated by the arrows.

Figure 5:
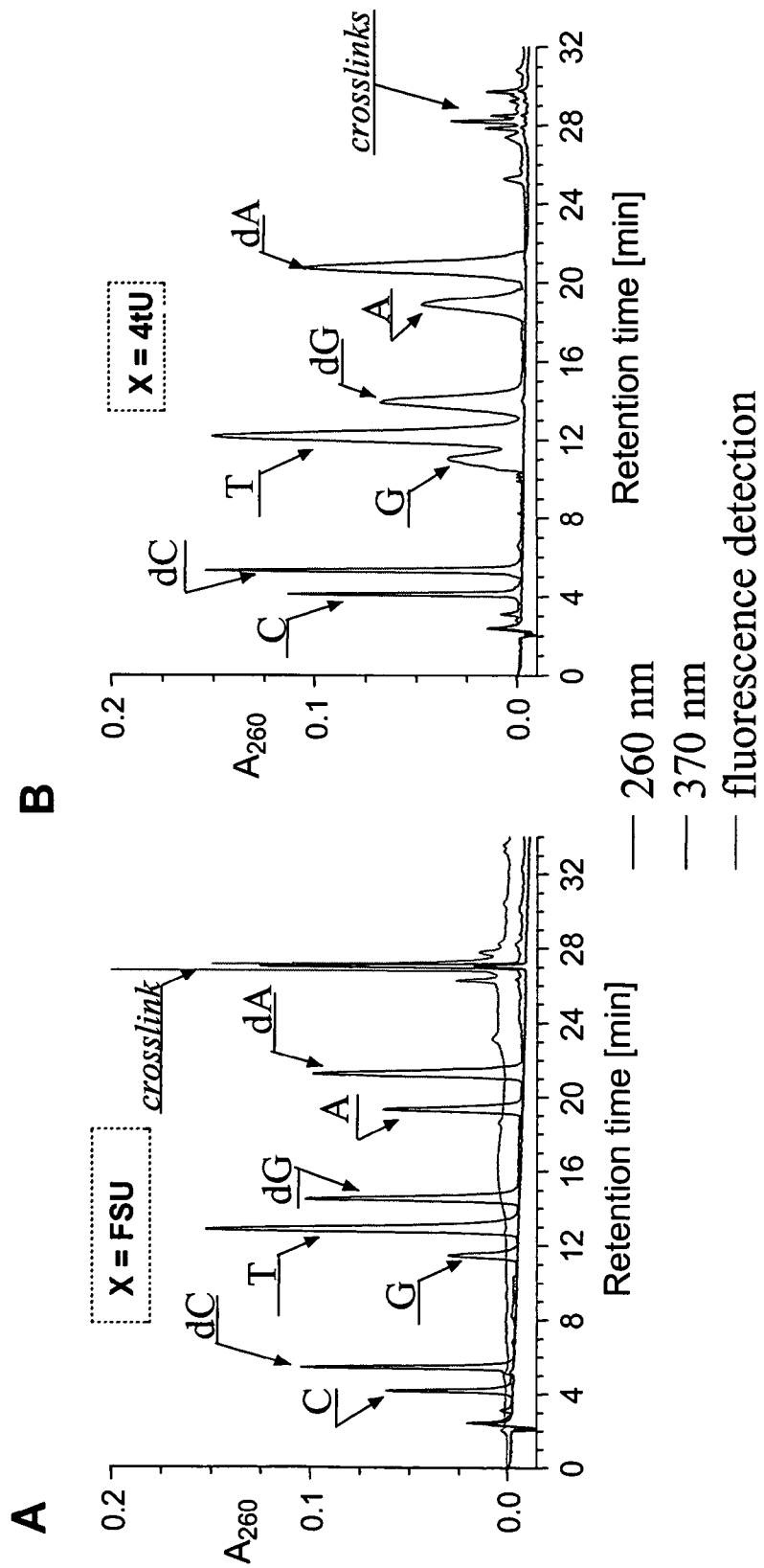
FIG. 5A is a high pressure liquid chromatography (HPLC) analysis of the enzymatic digestion of the crosslinked duplex of the dodecamer target sequence, 5'd-TTATCGTATC GT (SEQ ID NO: 1), and the pentamer probe, 5'-CGA(FSU)A (SEQ ID NO: 2). The peaks outlined by the lower heavy solid line (which is mostly flat) were detected at 370 nm. The peaks outlined by the upper heavy solid line were detected at 260 nm. The peaks indicated by the lighter line were detected by observation of fluorescence at 430 nm, after excitation at 370 nm. Peaks attributable to various nucleotides and deoxynucleotides and the peaks attributable to crosslinked products are indicated by the arrows and labels. X is the identity of the modified nucleotide (i.e., FSU).
FIG. 5B is a HPLC analysis of the enzymatic digestion of the crosslinked duplex of the dodecamer target sequence, 5'd-TTATCGTATC GT (SEQ ID NO: 1), and the pentamer control probe, 5'-CGA(4tU)A (SEQ ID NO: 3). The peaks outlined by the lower heavy solid line (which is mostly flat) were detected at 370 nm. The peaks outlined by the upper heavy solid line were detected at 260 nm. Peaks attributable to various nucleotides and deoxynucleotides and the peaks attributable to crosslinked products are indicated by the arrows and labels. X is the identity of the modified nucleotide (i.e., 4tU).

Enzymatic digestion of the crosslinked oligonucleotides with snake venom diesterase/alkaline phosphatase yielded a single trinucleotide adduct from the duplex formed using the 5-fluoro-4-thiouridine pentamer probe (SEQ ID NO: 2). See FIG. 5A. Digestion of the duplex formed using the 4-thiouridine pentamer control probe (SEQ ID NO: 3) gave a complex mixture of products and revealed no fluorescent product. See FIG. 5B.

Figure 6:
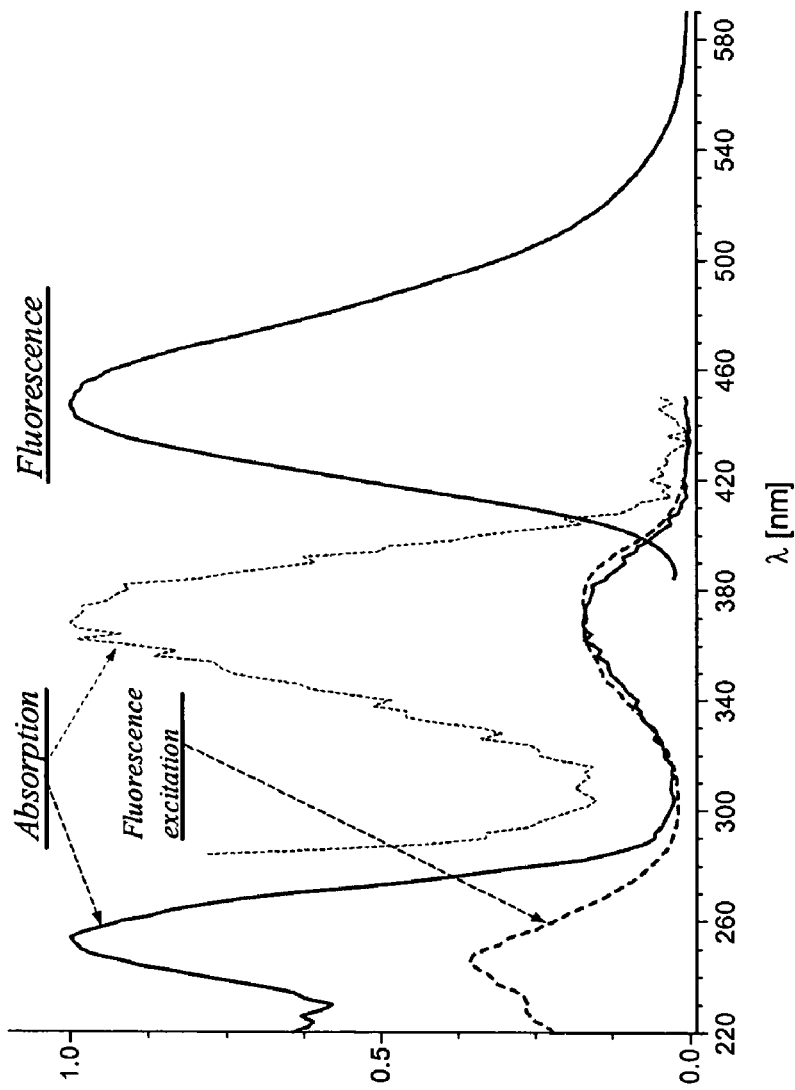
FIG. 6 is a fluorescence spectrum and a fluorescence excitation spectrum of the crosslinked product from the enzymatic digestion mixture shown in FIG. 5A.

A careful HPLC analysis of the digestion mixture of the crosslinked duplex of the target (SEQ ID NO: 1) with the 5-fluoro-4-thiouridine-containing pentamer probe (SEQ ID NO: 2) indicated that the photocrosslinking reaction involved one of the deoxythimidines that flank both sides of the deoxyadenosine residues in the target sequence. The deoxyadenosine residues are opposite to 5-fluoro-4-thiouridines in the probe sequences when the target is hybridized to the probe. The photoadduct released after enzymatic digestion appears to contain one of the two adenosines adjacent to the 5-fluoro-4-thiouridine on probe sequence (SEQ ID NO: 2). The fluorescence spectrum and the fluorescence excitation spectrum of the crosslink released during digestion are shown in FIG. 6.

Example 2

Interaction of a Decamer Probe Molecule with DNA

A decamer RNA probe was synthesized having the sequence 5'-CGA(FSU)ACGAUA (SEQ ID NO: 4). The corresponding decamer control probe having the sequence 5'-CGA(4tU)ACGAUA (SEQ ID NO: 5) was also synthesized. Solutions containing each of the decamer probes and the target (SEQ ID NO: 1) were made containing probe: target ratios of 1:1.1 in phosphate buffer at pH=7.0. The melt curves for the duplexes formed from the decamers (SEQ ID NO: 4 or SEQ ID NO: 5) and the target (SEQ ID NO: 1) are shown in FIGS. 7A and 7B. As in the case of the pentamer probes in Example 1, the melt curves of the two duplexes are similar.

FIG. 8A shows the fluorescence intensity of the crosslinked product formed following irradiation of the duplex of the decamer probe (SEQ ID NO: 4) and the target (SEQ ID NO: 1) for varying amounts of time, from 0 min to 150 min. FIG. 8B shows the HPLC chromatogram of the photocrosslinking reaction products, with and without fluorescence detection, formed from the duplex of the target sequence (SEQ ID NO: 1) and the decamer probe (SEQ ID NO: 4). The HPLC chromatogram of the photocrosslinked products from the irradiation of the duplex of the target (SEQ ID NO: 1) and the decamer control probe (SEQ ID NO: 5) are shown in FIG. 8C. No fluorescent crosslinked product was formed following irradiation of the duplex containing the decamer control probe (SEQ ID NO: 5).

HPLC chromatograms of the enzymatic digestion products from the photocrosslinked duplex of the target (SEQ ID NO: 1) and the decamer probe (SEQ ID NO: 4) are shown in FIG. 9A. Two highly fluorescent trinucleotide adducts are detected, having almost identical UV and fluorescence spectra to those of the photoadduct formed from irradiation of the duplex of the pentamer probe (SEQ ID NO: 2) and the target (SEQ ID NO: 1) in Example 1. The UV absorption and fluorescence spectra of the two photoadducts are presented in FIG. 10. HPLC analysis of the enzymatic digestion products from the photocrosslinked duplex of the decamer control probe (SEQ ID NO: 5) and the target sequence (SEQ ID NO: 1) is shown in FIG. 9B. Only a small amount of photoadduct and no fluorescent product was detected.

A second decamer probe sequence, 5'-CGATACGA (FSU)A (SEQ ID NO: 6), was synthesized. After hybridization of the second decamer probe (SEQ ID NO: 6) with the target (SEQ ID NO: 1) and subsequent irradiation, it was observed that the yield of crosslinked photoproduct can be increased by placing the modified nucleotide, 5-fluoro-4-thiouridine, in the position one base removed from the 3' end of the RNA decamer probe. In this case, as shown in FIG. 11B, the crosslink is formed in nearly quantitative yield after 40 minutes of irradiation with a estimated flux of <5 W/cm² using a 200 Waft high-pressure HBO® 200 mercury (Hg) lamp (OSRAM GmbH, Munich, Germany) equipped with a 366 nm interference filter As indicated in FIG. 11C, this photoproduct is highly fluorescent. Mass spectrometry and enzymatic digests are consistent with the formation of a photocrosslinkage that involves the 5-fluoro-4-thiouridine of the probe (SEQ ID NO: 6) and a thymidine in the target sequence (SEQ ID NO: 1) wherein the thymidine is adjacent to the adenine opposite the modified nucleotide in the hybrid duplex. Additionally, melt curves for the duplex, both before and after irradiation, show a shift of 15° C. in the melting curve of the irradiated duplex, indicative of strong interactions between the components of the duplex. See FIG. 12.

This is further evidence for the formation of a covalent bond between the members of the hybridized duplex.

Example 3

Reaction of 5-Fluoro-4-thiouridine with Thymidine

Scheme 3. Reaction of 5-Fluoro-4-thiouridine with Thymidine.

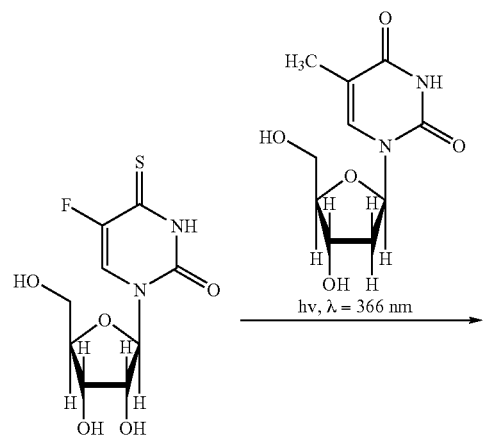

In order to obtain more detailed structural information on the fluorophore produced by irradiation of oligonucleotide duplexes, the reaction of 5-fluoro-4-thiouridine with thymidine was studied, as indicated in Scheme 3, above. A solution containing 2.5 mM 5-fluoro-4-thiouridine and 5.0 mM thymidine was prepared and irradiated by the 360 nm Hg line with a flux of <5 W/cm². The reaction was followed by comparison of the relative intensities of the 260 nm and 370 nm absorption bands of the nucleosides. See FIG. 13. Two photoproducts, 1 and 2, were observed by HPLC as shown in FIG. 14B. Photoproduct 1 has a shorter HPLC retention time. Matrix assisted laser desorption ionization time-of-flight (MALDI TOF) mass spectrometry indicated that both photoproducts have the same molecular formula, $C_{19}H_{24}N_4O_{10}S$, indicating that the photoaddition of the two nucleosides results in the formation of two isomeric photoadducts, accompanied by a loss of hydrogen fluoride (HF). Two possible structures for such photoproducts are shown in FIGS. 14C and 14D.

The two photoproducts were analyzed by absorbance and fluorescence spectroscopy. FIGS. 15A and 15B show the absorption and fluorescence emission spectra of the two isomeric photoproducts. Excitation at 360 nm produced emission with a $\lambda_{max}$ at 470 nm, with a quantum yield of 0.49±0.04 and 0.26±0.03 for isomers 1 and 2, respectively. The fluorescence lifetimes of isomers 1 and 2 were measured to be 14.2±0.7 ns and 7.3±0.5 ns, respectively.

For comparison, a control reaction using 4-thiouridine in place of 5-fluoro-4-thiouridine was performed. Crosslinking was observed, however, the reaction did not result in the formation of a fluorescent product.

Example 4

Fluorophore NMR Structural Studies

The structures of both isomeric photoproducts were established by NMR analysis. There are four possible isomers having the molecular formula of products 1 and 2, each having four diasteromers. The nomenclature for the atoms will derive from the name of the pyrimidine residues involved in the crosslinking reaction. The hydrogen and carbon atoms in the crosslinked molecule that derive from the thymidine on the target strand will be referred to as T-H# and T-C#, respectively, where the number (#) will indicate the ring position. In a similar manner, the hydrogen and carbon atoms in the crosslinked molecule that derive from the 5-fluoro-4-thiouridine on the probe strand will be referred to as FSU-H# and FSU-C#, respectively, where the number (#) will indicate the ring position.

The T-C5 methyl group (i.e., the methyl group at carbon 5 of the former pyrimidine ring) is cis to proton T-H6 (i.e., the proton at carbon 6 of the former thymidine ring) in two isomers and trans in the others. After irradiating protons of the methyl group, an NOE effect was observed on the T-H6 proton in differential NOE spectra recorded for both 1 (see FIG. 16A) and 2. These experiments provided unambiguous evidence that in both photoadducts, the methyl group and T-H6 protons are in a cis configuration. This fact, combined with the absence of a NOE to FSU-H6, reduced the number of possible isomers for the structures of products 1 and 2 to 2, further eliminating two of the possible diastereomers. The detailed proof of the photoproduct structure is described for isomer 1. The proof for the structure of isomer 2 is completely analogous.

The $^1$H and $^{13}$C NMR spectra of isomer 1 reveal that two sugar moieties, ribose and deoxyribose, are present in the structure. Their $^1$H and $^{13}$C signals were unambiguously assigned to specific sugars based on $^1$H—$^1$H COSY and $^1$H—$^{13}$C HSQC spectra. Apart from the sugar protons, the $^1$H NMR spectrum shows only three additional singlets at 8.3 ppm, 5.9 ppm and 1.7 ppm. The integrated intensities of these singlets corresponded to one, one, and three protons, respectively.

All 19 carbon signals can be identified in the $^{13}$C NMR spectrum, in agreement with the molecular formula. Aside from the ten carbons of the sugar residues, there are six quaternary carbon atoms, one methyl group at 17.2 ppm and two carbon atoms at 135.9 ppm and 64.9 ppm, that are directly bonded to protons at 8.3 ppm and 5.9 ppm, respectively. In order to establish the structure of the non-sugar portion of the molecule, long-range proton-carbon correlations in the $^1$H—$^{13}$C HMBC spectrum were analyzed. See FIG. 17. Cross-peaks observed in the $^1$H—$^1$H NOESY experiment were confirmatory for the structure.

The interconnection between two rings can be established from the detailed analysis of the $^1$H—$^{13}$C HMBC spectrum using the correlation of carbons and hydrogens via J(CH) coupling constants over two and three bonds. The proton signal at 5.9 ppm of the anomeric proton of the ribose correlates to signals at 155.9 ppm and 135.9 ppm in the $^1$H—$^{13}$C HMBC spectrum. The NOE observed between the anomeric proton and the peak at 8.3 ppm led to the assignment of that peak to the T-H6 proton of the pyrimidine ring of thymidine. The anomeric proton of deoxyribose exhibits a weak NOE effect to the proton at 5.9 ppm, which also has correlations to the carbon resonances at 64.9 ppm and 152.2 ppm in the $^1$H—$^{13}$C HMBC spectrum. The chemical shift of the proton at 5.9 ppm and its directly bonded carbon atom at 64.9 ppm, together with the observed correlation between the anomeric proton of the deoxyribose and the signal at 64.9 ppm in the $^1$H—$^{13}$C HMBC spectrum suggest that one of the covalent bonds formed during the photoreaction occurs at the T-C6 carbon of the thymidine pyrimidine ring.

The topology was established based on cross peaks connecting the two pyrimidine rings. Crosspeaks between the proton at 5.9 ppm and the carbon atoms at 55.5 ppm, 115.4 ppm, and 174.6 ppm, together with observed correlations between the methyl protons and carbon atoms at 55.5 ppm and 174.6 ppm indicated the structure shown in FIG. 17.

To further support the structure of the photoproduct, models were built of the two possible photoproducts that would be formed if one of the covalent linkages between the two nucleobase rings involved a (FSU-C5)-S-(T-C6) linkage or alternatively a (FSU-C4)-S-(T-C5) linkage, where S represents the sulfur atom. Analysis of the structures indicates that only the structure with the (FSU-C5)-S-(T-C6) linkage is possible. In the case of the other structure, a close contact between protons T-H6 and FSU-H6 should be detectable in an NOE-type spectra. Further, in the case of the structure with the (FSU-C4)-S-(T-C5) linkage, a strong cross peak between a methyl proton and the FSU-C4 atom should be absent in the $^1$H—$^{13}$C HMBC spectrum.

Example 5

Energetics Calculations

The photocrosslinking reaction that creates the fluorescent crosslinked product was modeled using energy minimization of the DNA-RNA heteroduplex structures formed between the decamer probe sequence, 5'-CGA(FSU)ACGAUA (SEQ ID NO: 4), and the dodecamer target sequence, 5' d-TTATCGTATC GT (SEQ ID NO: 1). Classical energy minimization was carried out using constraints to force the approach of 5-fluoro-4-thiouridine on the RNA stand to a thymidine (T) on the DNA strand. As shown in Scheme 4, there are two possible modified thymidine residues that can crosslink with 5-fluoro-4-thiouridine (shown in Scheme 4 as U*).

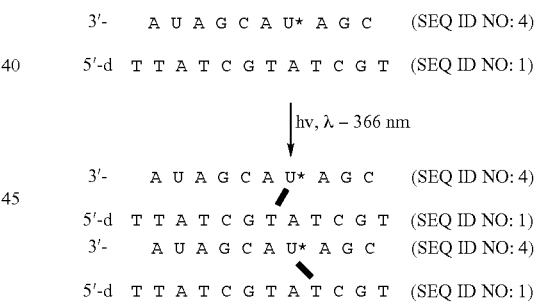

Models for the initial interactions of the 5-fluoro-4-thiouracil nucleotide with each of these two thymides are referred to as D2 and D4, depending on the location of the thymidine in the DNA sequence. These heteroduplexes were energy minimized with the following constraints:

D2=5F4S-U S(4)-D_2 C(6) and 5F4S-U C(4)-D_2 C(5)
D4=5F4S-U S(4)-D_4 C(6) and 5F4S-U C(4)-D_4 C(5)

Schematic representations for D2 and D4 are shown in FIGS. 18 and 19.

Subsequently, a heteroduplex model was created with a pseudo-cyclobutane ring (i.e., a four-membered ring containing three carbons and one sulfur) involving the above atoms (the sulfur and carbon 4 atoms from the modified uracil and carbons 5 and 6 from the thymidine). These models, D2_I and D4_I, are comprised of the pseudo-cyclobutane adduct with the thymidine in the 2- and 4-position, respectively. Finally, a rearranged crosslinked adduct was created that involved elimination of hydrogen fluoride. D2_F and D4_F are the crosslinked adducts with T in the 2- and 4-position, respectively. Once the energy minimizations were completed, excised base pair structures were used in DFT calculations to determine more accurate energies for the photochemical reaction pathway.

For the DFT calculations, models were excised from the energy minimized heteroduplexes discussed above. The phosphodiester bonds were removed and the resulting molecules were hydroxylated in the 3' and 5' positions. Excised models for D2 and D4 are shown in FIGS. 20A and 20B. Models of the excised pseudo-cyclobutane intermediates, D2_I and D4_I, are shown in FIGS. 21A and 21B. Models for the excised photoadducts, D2_F and D4_F, are shown in FIGS. 22A and 22B.

The optimized group state geometries and potential energy surfaces of D2, D4, D2_I, D4_I, D2_F, and D4_F were obtained using the GGA functional (see Perdew, J. P., et al., *Phys. Rev. B* 46, 6671-6687 (1992)) as implemented in Dmol3 (Molecular Simulations Inc., San Diego, Calif., United States of America). See Delley, B., *J. Chem. Phys.*, 113, 7756-7764 (2000). Geometry optimizations were carried out without constraints until the energy difference was less than $10^{-6}$ a.u. on subsequent iterations.

FIG. 23 shows the calculated thermodynamics of the photochemical reaction for the creation of one of the isomers (i.e., the one formed with the thymidine in the 2 position). In the energy diagram, TU2 refers to the ground state of the 5-fluoro-4-thiouridine, $T^1U2$ refers to the excited singlet state, $T^3U2$ refers to the excited triplet state, TU2_I refers to the pseudo-cyclobutane intermediate, and TU2__2 to the final photoadduct.

Energy calculations indicate that there is a conformational strain energy of approximately 18 kJ/mol and 64 kJ/mol for the close approach of the nucleotides of structures D2 and D4, respectively, when compared to an unconstrained RNA with the same sequence. The energies of the pseudo-cyclobutane bonded intermediates D2_I and D4_I are 114 kJ/mol and 83 kJ/mol, respectively, relative to the ground state. The energies of the two isomers of the final crosslinked product, D2_F and D4_F, are 54 kJ/mol and 67 kJ/mol, respectively, higher in energy than the starting configuration, showing that the photoproduct is not thermodynamically favored. However, the loss of HF in the intermediate step traps the molecule in a conformation that will form the fluorophore. Without being bound to any one theory, the driving force for the formation of the fluorescent crosslink appears to be loss of HF, since the HF bond energy of 616 kJ/mol more than compensates for the loss of the C—H and C—F bonds of the intermediate.

Example 6

Discussion of Experimental Results

The data described above provides evidence for a fluorescent crosslink between the modified uridine nucleotide, 5-fluoro-4-thiouridine (FSU), and thymidine (T). The crosslink is observed to occur with specificity when a T from an DNA strand is opposite to an adenine adjacent to the 5-fluoro-4-thiouridine residue in an RNA strand in a RNA:DNA hybrid. The high yield and specificity of the interstrand crosslinking reaction is combined with the fact that the photoproduct is fluorescent. Photocrosslinking between oligonucleotides and between nucleosides in solution provides two isomers. The fluorescence quantum yield ($\phi$) of one of the isomers is 0.49, sufficiently large to study hybridization events inside cells and on surfaces by observing the fluorescence of the crosslink. Computational studies indicate that having the T in the second position in the sequence of a target dodecamer sequence is more reactive because conformational distortion of the double-helix is smaller for the reaction with this thymidine than with a thymidine in the fourth position in the sequence.

Without being bound to any one theory, it is presumed that the energy required to make new bonds in the initial psuedo-cyclobutane intermediate formed upon irradiation of the duplex comes from the 5-fluoro-4-thiouridine excited state. The psuedo-cyclobutane intermediate is not observed experimentally, but is predicted by DFT calculations. DFT calculations show that the psuedo-cyclobutane intermediate is endothermic with respect to the distorted geometry, which is consistent with a photochemical mechanism.

Cyclobutane intermediates have been hypothesized for a variety of pairs of pyrimidine bases adjacent to one another in the base stack. See Tabaczynski, W. A., et al., *Biopolymers*, 50, 185-191 (1990); Gibbs, P. E. M., and Lawrence, C. W., *Nucleic Acids Res.*, 21, 4059-4065 (1993); and Kao, J. L. F., et al., *Chemical Research in Toxicology*, 6, 561-567 (1993). However, these pyrimidine dimers are all intrastrand crosslinks. The fact that the presently disclosed fluorescent crosslinked product is an interstrand crosslink that appears to involve a pseudo-cyclobutane intermediate is a unique feature.

The DFT calculations are validated by comparison with the stereochemistry of the structure determined by 2-D NMR. There are 16 possible diastereomers of the fluorescent crosslinked product, yet the two which were obtained structurally by NMR were also predicted by the classical energy minimization and DFT methods used. Interestingly, the structure determined for the fluorescent crosslinked product is not a planar molecule, but has an unusual bend angle of approximately 70°. The bend should weaken any πconjugation between the three rings of the molecule. Although it is a priori unexpected that such a geometry would give rise to a fluorescent molecule, the crosslinked product is an excellent fluorophore, and the approximately 14 ns lifetime is in a useful range for a variety of medical, biological, and other studies.

REFERENCES

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference.

Beaucage, S. L., and Iyer, R. P., *Tetrahedron*, 48, 2223-2311 (1992).

"Bioorganic Photochemistry: Photochemistry of the Nucleic Acids," Vol. 1, Morrison, H. ed., Wiley and Sons, New York, 1990.

Coleman, R. S., and Kesicki, E. A., *J. Am. Chem. Soc.*, 116, 11636-11642 (1994).

Delley, B., *J. Chem. Phys.*, 113, 7756-7764 (2000).

Favre, A., et al., *J. Photochem. Photobiol. B: Biol.* 42, 109-124 (1998).

Gibbs, P. E. M., and Lawrence, C. W., *Nucleic Acids Res.*, 21, 4059-4065 (1993).

Kao, J. L. F., et al., *Chemical Research in Toxicology*, 6, 561-567 (1993).

Kumar, R. K., and Davis, D. R., Nucleic Acids Res., 25, 1272-1280 (1997).

Lipsett, M. N., *J. Biol Chem.*, 240, 3975-3978 (1965).
Noll, D. M., et al., *Chem. Reviews*, 106, 277-301 (2006).
Norris, C. L., et al., *J. Am. Chem. Soc.*, 118, 5796-5803 (1996).
Perdew, J. P., et al., *Phys. Rev. B* 46, 6671-6687 (1992).
Tabaczynski, W. A., et al., *Biopolymers*, 50, 185-191 (1990).
Taras-Goślińska, K., et al., *J. Photochem. Photobiol. A: Chem.* 168, 227-233 (2004).
U.S. Pat. No. 4,973,679.
U.S. Pat. No. 5,026,838.
U.S. Pat. No. 5,142,047.
Wenska, G., et al., *J. Chem. Soc., Perkin Trans.* 1, 53-57 (2002).
Wenska, G., et al., *J. Org. Chem.*, 70, 982-988 (2005).
Zemlicka, J., et al., *Collect. Czech Chem. Commun.*, 29, 635 (1964).

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of determining the presence of a target nucleic acid molecule in a sample, said method comprising:

contacting a probe molecule with a sample comprising a target nucleic acid molecule, wherein the probe molecule comprises one or more 5-halo-4-thiouracil nucleobases, wherein each of the one or more 5-halo-4-thiouracil nucleobases is a 5-chloro-4-thiouracil nucleobase or a 5-fluoro-4-thiouracil nucleobase, and wherein the target nucleic acid comprises a thymidine;

irradiating the sample for a period of time at a wavelength at which the one or more 5-halo-4-thiouracil nucleobases is selectively photoexcited to form between a 5-halo-4-thiouracil nucleobase of the probe molecule and the thymidine of the target nucleic acid a fluorescent crosslinked product comprising a fluorophore having the structure of Formula (I):

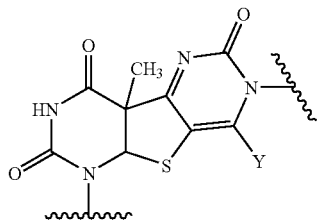

wherein Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and $R_4$ are selected from H and $C_1$-$C_5$ alkyl; and detecting the fluorescence of the fluorophore of Formula (I) at a chosen emission wavelength, thereby determining the presence of a target nucleic acid molecule in the sample.

2. The method of claim 1, wherein the probe molecule comprises an oligonucleotide sequence.

3. The method of claim 2, wherein the probe molecule hybridizes to the target nucleic acid in the sample to form an oligonucleotide duplex and irradiating the sample comprises irradiating the oligonucleotide duplex for a period of time to form one or more covalent bonds between the probe molecule and the target nucleic acid to form the fluorescent crosslinked product.

4. The method of claim 3, wherein each of the one or more 5-halo-4-thiouracil nucleobases comprises a structure of formula (II):

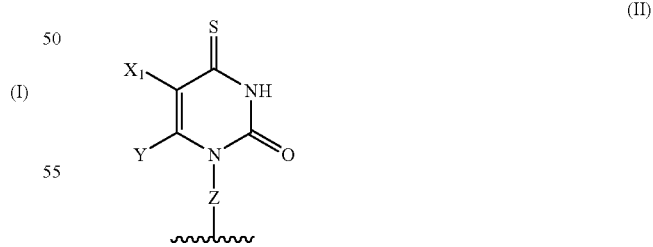

wherein:

$X_1$ is chloro or fluoro;

Y is selected from the group consisting of H, $C_1$-$C_5$ linear or branched alkyl, cyano, nitro, carboxy, —$NR_1R_2$, —$C(O)R_3$, and —NH—C(O)—$R_4$, wherein $R_1$, $R_2$, $R_3$, and $R_4$ are selected from H and $C_1$-$C_5$ alkyl; and Z is selected from the group consisting of ribose, 2'-deoxyribose, 2'-O-methyl ribose and morpholino.

5. The method of claim 4, wherein Y is H.

6. The method of claim 5, wherein the one or more 5-halo-4-thiouracil nucleobases are independently 5-fluoro-4-thiouridine or 5-chloro-4-thiouridine.

7. The method of claim 3, wherein at least one of the one or more 5-halo-4-thiouracil nucleobases is located adjacent to at least one adenine in the oligonucleotide sequence of the probe molecule.

8. The method of claim 3, wherein the contacting step takes place in a cell.

9. The method of claim 3, wherein both the probe molecule and the target nucleic acid are in solution.

10. The method of claim 3, wherein either the target nucleic acid or the probe molecule is immobilized on a solid support.

11. The method of claim 10, wherein the solid support is selected from the group consisting of a flat surface, a bead, a resin, a gel, a microsphere, a well, a microtiter plate, and a fiber.

12. The method of claim 3, further comprising determining an amount of the target nucleic acid in the sample.

13. The method of claim 3, further comprising separating the oligonucleotide duplex containing the fluorescent covalent crosslinked product from non-duplexed nucleic acids and non-duplexed probe molecules following the irradiating step.

14. The method of claim 3, wherein there is zero background fluorescence at the chosen emission wavelength prior to performing the irradiation step.

15. The method of claim 1, wherein the irradiating step is performed at a wavelength longer than about 280 nanometers.

16. The method of claim 15, wherein the irradiating step is performed with a UV light source.

17. The method of claim 3, further comprising amplifying one or more nucleic acid in the sample prior to contacting the probe molecule with the sample.

18. The method of claim 3, wherein the oligonucleotide sequence of the probe molecule is at least 70% complementary to the target nucleic acid.

19. The method of claim 3, wherein the oligonucleotide sequence of the probe molecule is 10 or more nucleotides in length.

20. The method of claim 19, wherein the oligonucleotide sequence of the probe molecule is 10 to 50 nucleotides in length.

21. The method of claim 19, wherein the oligonucleotide sequence of the probe molecule is 50 to 100 nucleotides in length.

22. The method of claim 19, wherein the oligonucleotide sequence of the probe molecule is greater than 100 nucleotides in length.

23. The method of claim 3, wherein the target nucleic acid is selected from the group consisting of animal, bacterial, fungal, human, parasitic, plant and viral nucleic acids.

24. The method of claim 3, wherein the target nucleic acid is selected from the group consisting of genomic DNA and cDNA.

25. The method of claim 24, wherein determining the presence of a target nucleic acid determines the presence of a gene or of foreign DNA in a cell.

26. The method of claim 3, wherein the sample is selected from the group consisting of a biological sample and an environmental sample.

27. The method of claim 26, wherein the biological sample is selected from the group consisting of a living cell, a fixed cell, a cell extract, a tissue, a tissue extract, blood, plasma, saliva, and urine.

28. The method of claim 27, wherein the biological sample is from a mammalian subject.

29. The method of claim 26, wherein the environmental sample is selected from the group consisting of tap water, waste water, well water, river water, lake water, soil, air and material collected from household surfaces.

30. The method of claim 3, wherein determining the presence of a target nucleic acid is indicative of one of the presence of a disease, the absence of a disease, the potential future presence of a disease, the progression of a disease, the regression of a disease, and combinations thereof.

31. The method of claim 3, wherein determining the presence of a target nucleic acid is indicative of the presence of one of the group consisting of a virus, a bacteria, a fungus, a parasite, and combinations thereof.

32. The method of claim 3, further comprising two or more probe molecules, wherein each of the two or more probe molecules comprises an oligonucleotide sequence at least 70% complementary to a different target nucleic acid.

33. The method of claim 32, wherein each of the two or more probe molecules is immobilized at a different discrete, known location on a solid support.

34. The method of claim 1, wherein the probe molecule is a 5-halo-4-thiouridine.

35. A fluorophore comprising a structure of Formula (I):

(I)

wherein:
Y is selected from the group consisting of H, $C_1$-$C_5$ linear or branched alkyl, cyano, nitro, carboxy, —$NR_1R_2$, —C(O)$R_3$, and —NH—C(O)—$R_4$, wherein $R_1$, $R_2$, $R_3$, and $R_4$ are selected from H and $C_1$-$C_5$ alkyl.

36. The fluorophore of claim 35, wherein the structure of Formula (I) is a structure of Formula (Ia):

(Ia)

wherein:
Y is selected from the group consisting of H, $C_1$-$C_5$ linear or branched alkyl, cyano, nitro, carboxy, —$NR_1R_2$, —C(O)$R_3$, and —NH—C(O)—$R_4$, wherein $R_1$, $R_2$, $R_3$, and $R_4$ are selected from H and $C_1$-$C_5$ alkyl;
$A_1$ is selected from a sugar, a protected sugar, a partially protected sugar, and a nucleic acid; and
$A_2$ is selected from a sugar, a protected sugar, a partially protected sugar, and an oligonucleotide.

37. The fluorophore of claim 36, wherein $A_1$ is a gene or a cDNA, and $A_2$ is an oligonucleotide.

38. The fluorophore of claim 37, wherein $A_1$ and $A_2$ are at least 70% complementary.

39. The fluorophore of claim 37, wherein the fluorophore is formed following irradiation of a fluorophore precursor comprising a hybridized duplex.

40. The fluorophore of claim 37, wherein the fluorophore is formed following irradiation of a fluorophore precursor comprising a hybridized duplex that comprises an oligonucleotide comprising a 5-halo-4-thiouracil nucleobase adjacent to an adenine.

41. A method of determining the presence of a target nucleic acid molecule in a sample, said method comprising:

contacting a probe molecule with a sample comprising a target nucleic acid, wherein the probe molecule comprises one or more 5-halo-4-thiouracil nucleobases wherein each of the one or more 5-halo-4-thiouracil nucleobases is a 5-chloro-4-thiouracil nucleobase or a 5-fluoro-4-thiouracil nucleobase, and wherein the target nucleic acid comprises a pyrimidine group, wherein the pyrimidine group comprises a natural uracil or thymine nucleobase;

irradiating the sample for a period of time at a wavelength at which the one or more 5-halo-4-thiouracil nucleobases is selectively photoexcited to form between the 5-halo-4-thiouracil of the probe molecule and the natural uracil or thymine nucleobase of the target nucleic acid a fluorescent crosslinked product; and detecting the fluorescence of the fluorescent crosslinked product formed between the 5-halo-4-thiouracil of the probe molecule and the natural uracil or thymine nucleobase of the target nucleic acid at a chosen emission wavelength, thereby determining the presence of a target nucleic acid molecule in the sample.

42. The method of claim 41, wherein the target nucleic acid molecule is a ribonucleotide or a polymer thereof and comprises a natural uracil nucleobase.

\* \* \* \* \*

SEQUENCE LISTING

<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: Artificially synthesized oligonucleotide

<400> SEQUENCE: 1
ttatcgtatc gt                                                          12

<210> SEQ ID NO 2
<211> LENGTH: 5
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: modified_base
<222> LOCATION: (4)..(4)
<223> OTHER INFORMATION: u is 5-fluoro-4-thiouridine

<400> SEQUENCE: 2 cgaua                                                                   5

<210> SEQ ID NO 3
<211> LENGTH: 5
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: modified_base
<222> LOCATION: (4)..(4)
<223> OTHER INFORMATION: u is 4-thiouridine

<400> SEQUENCE: 3 cgaua                                                                   5

<210> SEQ ID NO 4
<211> LENGTH: 10
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: modified_base
<222> LOCATION: (4)..(4)
<223> OTHER INFORMATION: u is 5-fluoro-4-thiouridine

<400> SEQUENCE: 4
cgauacgaua                                                             10

```
<210> SEQ ID NO 5
<211> LENGTH: 10
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: modified_base
<222> LOCATION: (4)..(4)
<223> OTHER INFORMATION: u is 4-thiouridine

<400> SEQUENCE: 5
cgauacgaua                                                                10

<210> SEQ ID NO 6
<211> LENGTH: 10
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: modified_base
<222> LOCATION: (9)..(9)
<223> OTHER INFORMATION: u is 5-fluoro-4-thiouridine

<400> SEQUENCE: 6
cgatacgaua                                                                10
```